(12) United States Patent
John et al.

(10) Patent No.: US 10,751,535 B2
(45) Date of Patent: Aug. 25, 2020

(54) SYSTEMS AND METHODS FOR ASSESSING PELVIC FLOOR DISORDER THERAPY

(71) Applicant: EBT MEDICAL, INC., Toronto (CA)

(72) Inventors: Michael Sasha John, Larchmont, NY (US); Paul B. Yoo, Toronto (CA)

(73) Assignee: EBT Medical, Inc., Toronto, Ontario (CA)

( * ) Notice: Subject to any disclaimer, the term of this patent is extended or adjusted under 35 U.S.C. 154(b) by 0 days.

(21) Appl. No.: 15/956,076

(22) Filed: Apr. 18, 2018

(65) Prior Publication Data

US 2018/0296834 A1    Oct. 18, 2018

Related U.S. Application Data

(60) Provisional application No. 62/486,969, filed on Apr. 18, 2017.

(51) Int. Cl.
*A61N 1/36* (2006.01)
*A61N 2/00* (2006.01)
(Continued)

(52) U.S. Cl.
CPC ........ *A61N 1/36007* (2013.01); *A61B 5/4836* (2013.01); *A61N 1/0456* (2013.01); *A61N 1/0476* (2013.01); *A61N 1/36031* (2017.08); *A61N 2/006* (2013.01); *A61B 5/0492* (2013.01); *A61B 5/04882* (2013.01); *A61B 5/1107* (2013.01); *A61B 5/1121* (2013.01);
(Continued)

(58) Field of Classification Search
CPC .. A61N 1/36007; A61N 2/006; A61N 1/0476; A61N 1/0456; A61N 1/36021; A61N 1/36135; A61N 1/36017; A61N 1/36031; A61B 5/4836; A61B 5/04882; A61B 5/0492; A61B 5/1107; A61B 5/1121; A61B 5/224; A61B 5/4041
See application file for complete search history.

(56) References Cited

U.S. PATENT DOCUMENTS

| | | | |
|---|---|---|---|
| 8,406,886 B2* | 3/2013 | Gaunt | A61B 5/0028 607/148 |
| 2010/0217349 A1* | 8/2010 | Fahey | A61F 7/10 607/48 |

(Continued)

*Primary Examiner* — Amanda K Hulbert
*Assistant Examiner* — Natasha Patel
(74) *Attorney, Agent, or Firm* — Rosenberg, Klein & Lee

(57) ABSTRACT

Systems and methods provide stimulation of peripheral targets such as targets in the lower limbs. Electrode arrays realized in circumferential or longitudinal embodiments have pads with horizontal and/or vertical offsets. Electrode array geometries are customizable and adaptable to individual users and treatment of different disorders. Novel systems of customization include software and hardware implemented solutions. A single device can provide treatment of two or more disorders or unwanted states using selected electrode geometries and stimulation protocols. Systems and methods for assessment of candidate stimulation sites and protocols use subjective or objective measures or both to determine which meet stimulation success criteria. Simulation is provided using transcutaneous, percutaneous, or implantable stimulators. A main advantage is the improved treatment of pelvic floor disorders, and especially overactive bladder (OAB).

20 Claims, 12 Drawing Sheets

(51) Int. Cl.
*A61N 1/04* (2006.01)
*A61B 5/00* (2006.01)
A61B 5/22 (2006.01)
A61B 5/0492 (2006.01)
A61B 5/11 (2006.01)
A61B 5/0488 (2006.01)

(52) U.S. Cl.
CPC .............. *A61B 5/224* (2013.01); *A61B 5/4041* (2013.01); *A61N 1/36017* (2013.01); *A61N 1/36021* (2013.01); *A61N 1/36135* (2013.01)

(56) References Cited

U.S. PATENT DOCUMENTS

| | | | | |
|---|---|---|---|---|
| 2014/0046423 A1* | 2/2014 | Rajguru | ............... | A61N 1/0456 607/144 |
| 2014/0163644 A1* | 6/2014 | Scott | .................. | A61N 1/36139 607/60 |
| 2015/0148878 A1* | 5/2015 | Yoo | ...................... | A61N 1/0472 607/118 |

* cited by examiner

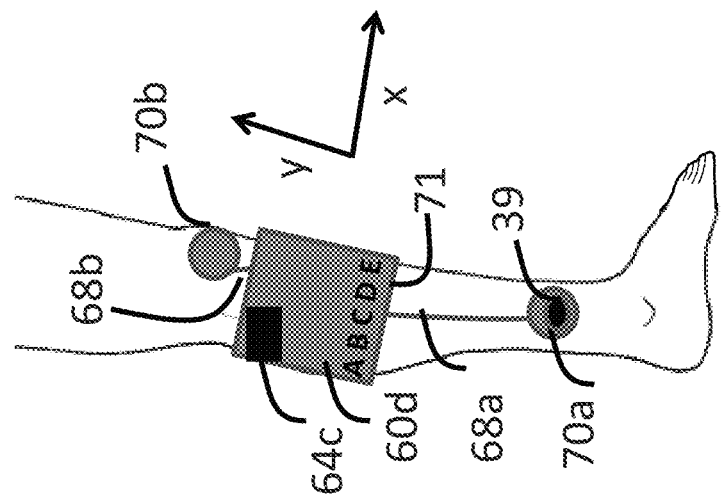
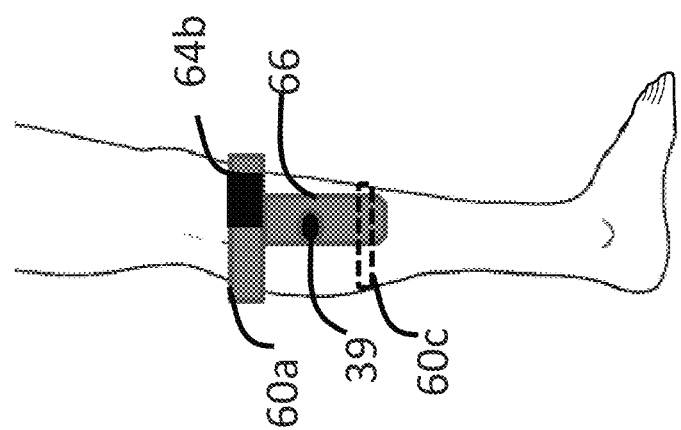
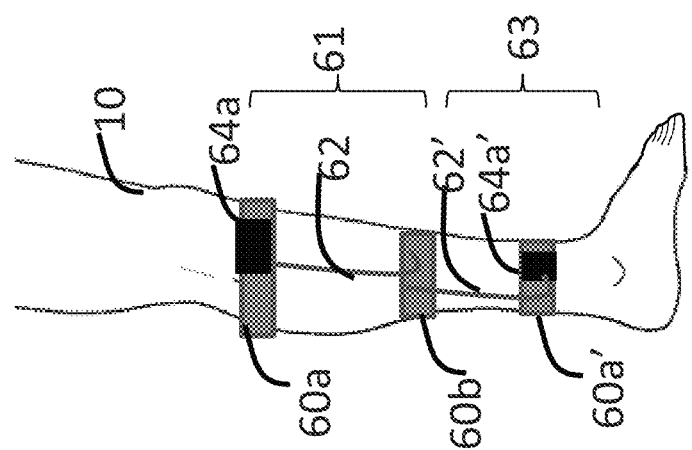

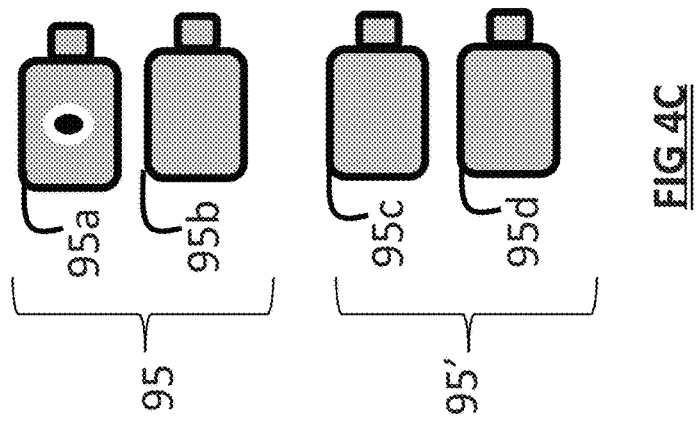
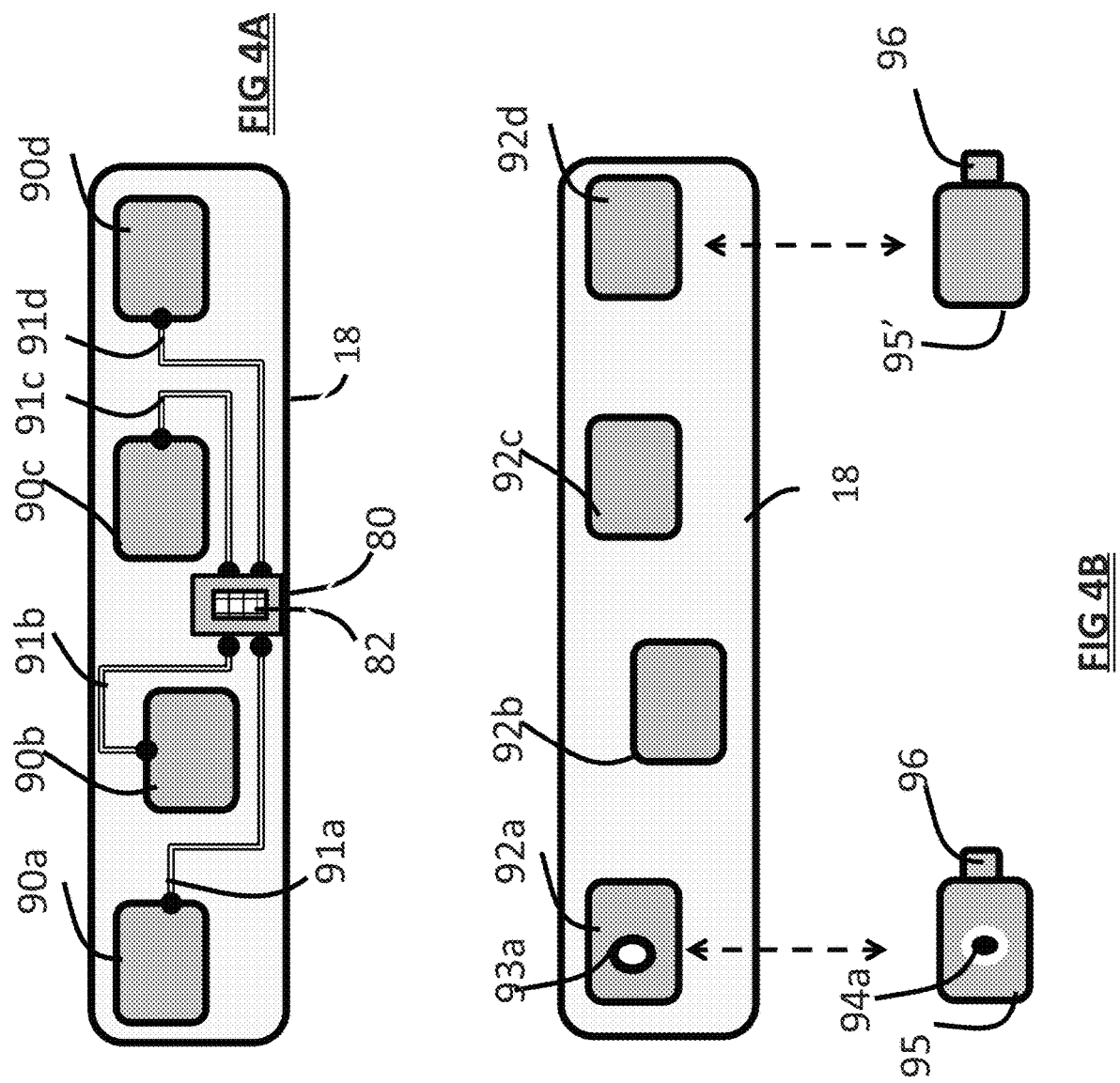

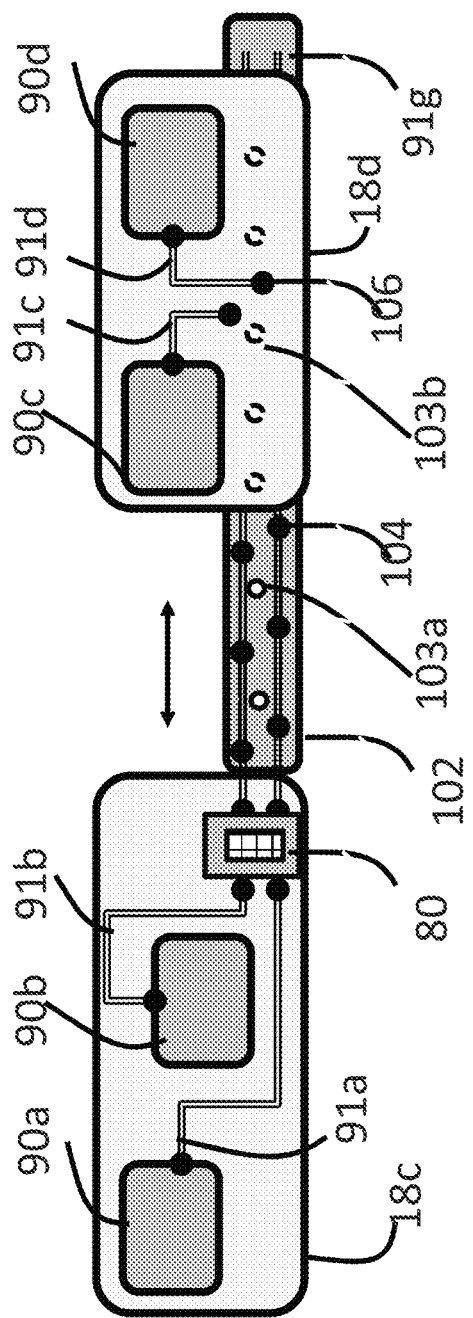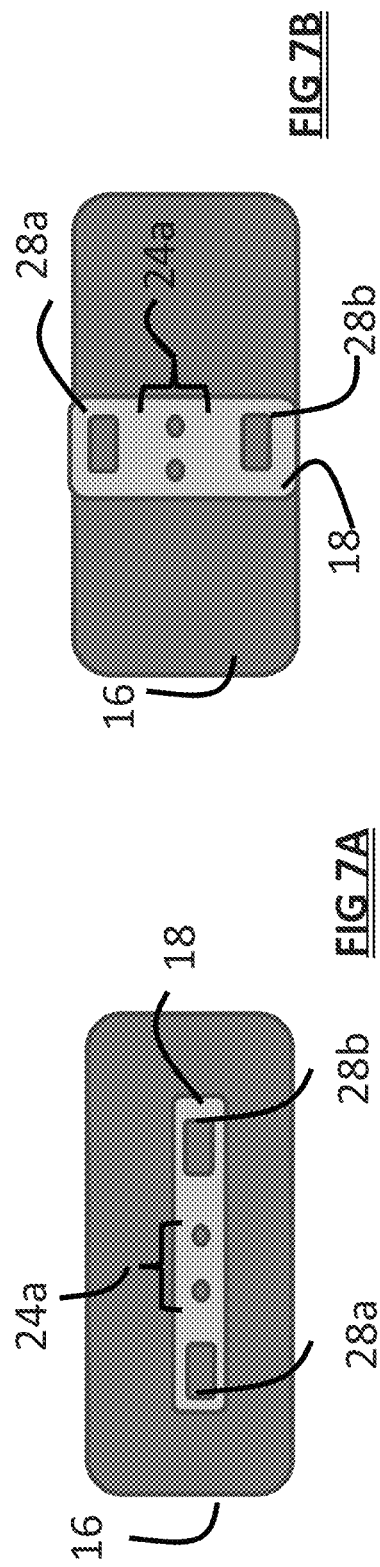

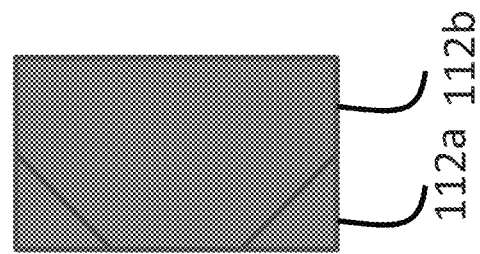
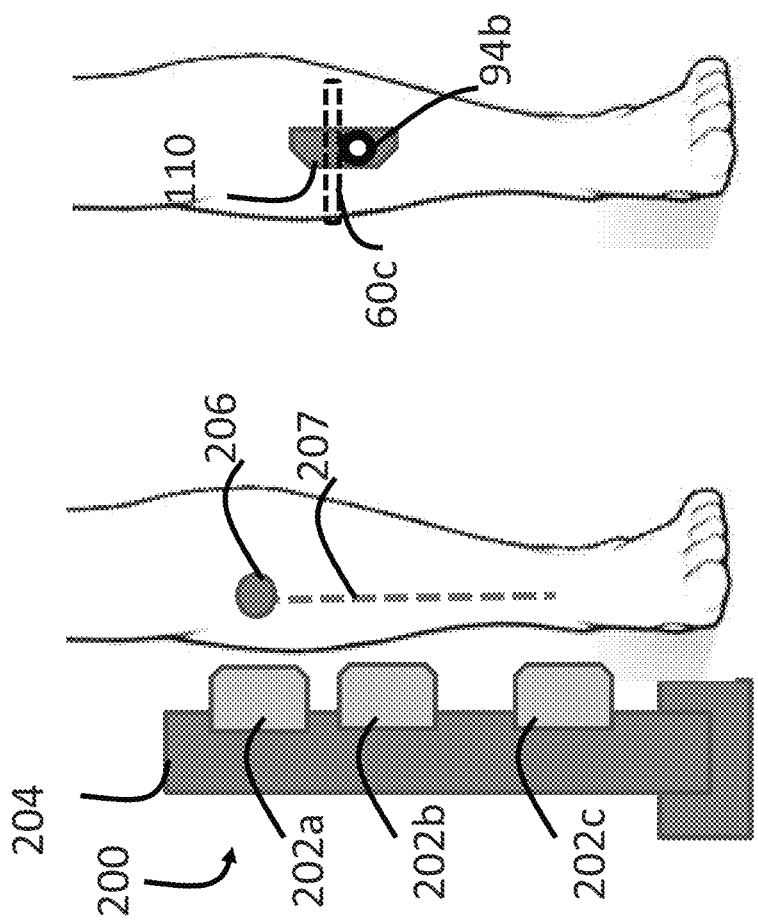

SYSTEMS AND METHODS FOR ASSESSING PELVIC FLOOR DISORDER THERAPY

REFERENCE TO PENDING PRIOR PATENT APPLICATIONS

This patent application claims benefit of provisional application 62/486,969 filed 18 Apr. 2017.

The above-identified patent applications are hereby incorporated herein by reference.

FIELD OF THE INVENTION

This invention relates generally stimulation of peripheral nerves to provide therapy and symptomatic relief disorders such as pain, overactive bladder, and other disorders.

BACKGROUND OF THE INVENTION

Electrical stimulation can be advantageous over drug therapy because it can avoid the resulting side-effects. Further, patients who are refractory to, or non-compliant with, drug therapy may benefit from electrical stimulation. A method of treatment which includes providing peripheral stimulation in combination with drug therapy may allow for therapy benefit to be obtained with lower dosages or may allow some patients to obtain sufficient benefit from the combination therapy (while this does not occur when the drug is provided without peripheral stimulation), or may otherwise provide greater symptom relief to the patient.

Transcutaneous Electrical Nerve Stimulation (TENS) methods and devices apply electrical currents to the skin in order to modulate underlying target tissue such as muscles and nerves. TENS systems deliver energy through a patient's skin with two or more surface electrodes that do not pierce the skin. This is considered less invasive than percutaneous electrical nerve stimulation (PENS) or implantable systems. TENS is commonly used in the treatment of, or amelioration of, symptoms related to acute and chronic pain. Diabetic peripheral neuropathy, and associated pain in the foot or lower leg, is an example of a disorder that may be treated by TENS of the lower leg. This site of pain is often proximate, or caudal, to the site of stimulation. However, TENS in the lower leg may, in turn, stimulate targets in the spine or brain, which may allow such benefit as treating lower back pain.

In TENS, electrodes are applied to a person's skin at a target area which is selected to allow the stimulation to produce desired effects. For treatment of pain or muscle stimulation the electrodes may be applied at candidate stimulation locations by an individual user or doctor until the symptom relief is obtained. Typically low current (generally less than 50-100 mA) and short duration pulses (e.g. 50-200 μsec) are applied at frequencies between about 1 and 200 Hz, although the frequencies in the 50 kHz range may also be used. The shape of the pulses can be monophasic or biphasic (e.g., charge balanced). In the case of PENS or magnetic stimulation, candidate stimulation site(s) can be similarly evaluated to assess a treatment site prior to treatment being provided.

Generic TENS devices usually include a pulse generator which connects to at least one set of 2 electrodes, each of which connected to the generator using wires. Additionally, a set may include 3 electrodes where 2 electrodes serve as anode and one electrode serves as cathode, or vice versa. The anode and cathode designations can be determined dynamically, and the assignment can instantaneously change during the provision of stimulation such as when using biphasic waveforms. Additionally, more than one pair or set of electrodes can be used and independently controlled by separate circuitry of the pulse generator. Generic TENS systems provide for flexibility, but may have disadvantages such as requiring some time and effort to set up correctly. Generic TENS systems may necessitate patient training and/or supervision by a doctor. There is a risk of electrodes being placed incorrectly.

Various disadvantages have been overcome by specialized TENS systems that are designed to treat disorders such as pain, migraine, tremor, high blood pressure, sleep, etc. These systems provide features such as: a) using electrodes provided at fixed inter-electrode distances and geometries by incorporating these into a fixed substrate or electrode array, b) using support structures designed to secure stimulation electrodes in place, and c) using software and hardware components that assist with providing therapy in a correct manner (e.g., ensuring the impedance is not too high before or during provision of therapy, automatically setting of stimulation parameters, etc.).

An example system is disclosed in patent U.S. Pat. No. 8,948,876 (incorporated by reference herein), entitled "Apparatus and method for relieving pain using transcutaneous electrical nerve stimulation" which is designed for the treatment of pain. Improved pain relief is provided using a TENS device is configured to assist with setting the stimulation intensity above an individual's sensory threshold. Nerve recruitment threshold is not disclosed and may be higher than this cutaneous sensory threshold.

In peripheral nerve stimulation therapy, the selection of an appropriate stimulation parameter value (e.g., amplitude) requires that stimulation is below an intensity level that causes moderate discomfort or pain. However, it is also critical that sufficient electrical activation of therapeutically-relevant nerve fibers is achieved in patients. For example, in the case of PENS or TENS stimulation of the posterior tibial nerve, the location and amplitude of stimulation is considered successful when the set up creates a motor evoked response (foot twitch or fanning out of the toes) is achieved. The "successful" stimulation parameters are different for different people and can be different for the same person on different stimulation sessions that occur at different times or days. This may also be true within the same stimulation session. Although a TENS device can be set to gradually and automatically increases stimulation intensity to a programmed target level that previously was found to be suitable for a patient, that level may not be good for subsequent treatments due to variation in patient sensitivity, or changes in electrode contact, impedance, and/or location. The clinical utility of regulating stimulation parameters, such as stimulus intensity, based on an electrical impedance signal of this approach is unclear. Various additional methods of assessing, or re-assessing, sufficient stimulation amplitude may thus be helpful in improving therapy.

Additionally, determining subjective sensory experience related to successful candidate sites or nerve recruitment thresholds may require feedback from a patient. In the case of PTN stimulation, successful sites and parameters may be assessed by motor responses in the foot. However, stimulation of SAFN has been found by the inventors not to be accompanied by this type of response. Instead a patient subjectively reports experiencing a sensation associated with nerve recruitment. When implantation is done using an anesthetic, intra or post-surgical assessment can possibly be made which includes patient assessment of the stimulation with respect to sensation. However, even local anesthetic may prevent accurate patient feedback in the peri-procedural window.

Accurate reporting of stimulation-evoked sensation may be difficult or impossible in some patients. This may be more challenging in older, diabetic, or cognitively impaired patients. In patients the SAFN may indeed be electrically activated, but some patients will not detect any sensation related to stimulation. Some patients may only experience a stimulation field adjacent to the electrode that fails to indicate proper nerve recruitment for nerves such as the SAFN. As a result, it may be difficult for a patient to provide accurate and reliable feedback that will facilitate the determination, selection or confirmation of therapeutically effective stimulation parameters and locations for electrode placement. Additionally, patient feedback may not allow robust selection between two candidate locations or protocols.

There is a need for a new and improved peripheral stimulation devices which address the issues and shortcomings associated with prior art devices, and especially in relation to provision of therapy for overactive bladder.

SUMMARY OF THE INVENTION

In a preferred embodiment, a TENS system comprises a stimulator device designed to provide stimulation in the region of an individual's knee or upper calf and includes a pre-configured electrode array with one or more electrodes designed to provide at least one of: stimulation to a target area near a circumferentially disposed electrode; stimulation to a target area both at and below or above a circumferentially disposed electrode; stimulation that is approximately semi-circumferential; or stimulation that is approximately fully circumferential.

With respect to the treatment of overactive bladder, the stimulation electrodes may be positioned so that at least one electrode targets the medial aspect of the leg, or two or more electrodes target the medial aspect of the leg, or one electrode targets the saphenous nerve on the medial aspect of the leg and the other targets the sural nerve on the lateral aspect of the leg, and stimulation parameters are provided which allow for the treatment of overactive bladder.

With respect to the treatment of overactive bladder, the stimulation electrodes may be positioned so that at least one electrode targets the medial aspect of the leg at or below the level of the knee but above the calf, or two or more electrodes target this area, and at least one additional electrode is also positioned above the medial malleolus at a location which targets the posterior tibial nerve, and stimulation parameters are provided which allow for the treatment of overactive bladder.

In an embodiment a first electrode stimulation circuit is configured to stimulate both the saphenous nerve and the sural nerve using a first set of stimulation parameters sufficient to provide nerve activation, at an amplitude that is also set sufficiently low to be comfortable to an individual and within a frequency and amplitude range found to produce bladder inhibition.

In an embodiment a first electrode stimulation circuit is configured to stimulate the saphenous nerve using a first set of stimulation parameters, at a first amplitude that is set low enough to be comfortable to an individual and high enough produces an electrotactile or "paresthesia" sensation, and a second electrode stimulation circuit is configured to stimulate the sural nerve using a second set of stimulation parameters, at a second amplitude that is set to be low enough to be comfortable to an individual and high enough to produce at least a cutaneous sensation.

In an embodiment a first electrode stimulation circuit is configured to stimulate the saphenous nerve using a first set of stimulation parameters, at a first amplitude that is set to be comfortable to an individual and sufficient to provide cutaneous sensation.

In an embodiment a first electrode stimulation circuit is configured to stimulate the sural nerve using a first set of stimulation parameters, at a first amplitude that is set to be comfortable to an individual and which has been found to be effective in the treatment of overactive bladder disorder, such as between 1 and 50 Hz.

An advantage of the disclosed invention is that the TENS device and at least one associated configuration of an electrode array, are designed for easy, rapid, and clinically useful placement of the electrode array by an individual seeking treatment for overactive bladder. Further, in embodiments, the system may be configured, or reconfigured, for treatment of either overactive bladder or pain relief in the feet and/or lower legs. Accordingly, there may be at least two different software modules and one, two or more different electrode arrays which allow for the treatment of overactive bladder, pain, or both to be provided. Further, there may be provided software which controls which electrodes of the array are used to provide stimulation to provide treatments for different disorders, and which can be configured to allow a patient to switch between protocols and electrode sets used to deliver therapy depending upon what therapy is being used to treat the patient.

In a further embodiment the system can be configured to provide combination stimulation of both the saphenous and the PTN and a sufficient number of electrodes can be provided to allow for this treatment flexibility.

In a further embodiment the system can be configured to increase the size of the stimulation field that is used to provide relief in the treatment of pain by using electrodes in addition to those provided on an array that is disposed in a circumferential manner.

In a further embodiment therapeutic intensity can be adjusted, and reassessed/readjusted in various automatic or semi-automatic manners and the patient can also further adjust the stimulation intensity as needed.

In a further embodiment therapeutic intensity can be adjusted in various settings which relate to the patient being able to feel tactile or other sensations provided by various types of stimulators such as vibration stimulators, which may also be provided in the presence of heat or cold.

In a further embodiment of the system, the therapeutic intensity can be adjusted to be higher than that which is obtained in the absence of a sensory mask, such as a vibrational, sonic, a source of heat or cold, or other type of stimulation.

In a further embodiment of the system the stimulation protocol can be changed to deter, compensate for, or take advantage of sensory changes such as habitation. For example, the treatment intensity can slowly be increased in the second half of a treatment after the subject has habituated. Additionally, pauses or slowly varying changes in the stimulation protocol may be used as part of the protocol. This can occur in a user selected programmable manner or via a default protocol.

In a further embodiment of the system the stimulation protocol can contain an assessment protocol where the stimulation parameters are varied in order to increase the ability of a subject to assess whether they feel the stimulation and assess whether electrodes are positioned correctly, such as for stimulation of the saphenous nerve, and then the stimulation can remain constant, or vary over a lower range of intensity, during the treatment portion of the therapy.

These and various additionally disclosed embodiments can provide advantages related to increasing therapy effectiveness and user friendliness of the systems, increasing patient compliance, and decreasing any interference with the patient's normal daily activities.

BRIEF DESCRIPTION OF THE DRAWINGS

These and other objects and features of the present invention will now be more fully disclosed by the following detailed description of the preferred embodiments of the invention, which is to be considered together with the accompanying abstract, claims, and drawings wherein like numbers refer to like parts, and further wherein:

FIGS. 3A-3C are schematic views showing additional embodiments of TENS systems mounted to a lower leg of a patient;

FIG. 4A is a schematic view of the back side of an example electrode array such as can be used with the TENS apparatus of FIG. 1A;

FIG. 4B is a schematic view of the front side of an example electrode array such as can be used with the TENS apparatus of FIG. 1A, and also shows TENS electrode accessories to be used with the array;

FIG. 4C is a schematic view of the front sides and back sides of two types of TENS electrode accessories to be used with the array;

FIG. 6C is a schematic view of an array with a track that allows for setting an adjustable distance between electrodes.

FIGS. 7A-7B are schematic views of two different electrode array configurations which can be used with the TENS apparatus of FIG. 1A to provide horizontally or vertically oriented stimulation patterns;

FIG. 10 shows a system for providing magnetic stimulation of the lower leg in the treatment of overactive bladder.

FIG. 11A shows an embodiment of an external stimulator configured for stimulation of the saphenous nerve.

FIG. 11B shows an embodiment of a TENS electrode having conductive and non-conductive sections.

DETAILED DESCRIPTION OF THE INVENTION

In the following description, sections headers are provided for convenience and readability and do not limit the invention in any manner.

Figures 1A, 1B:
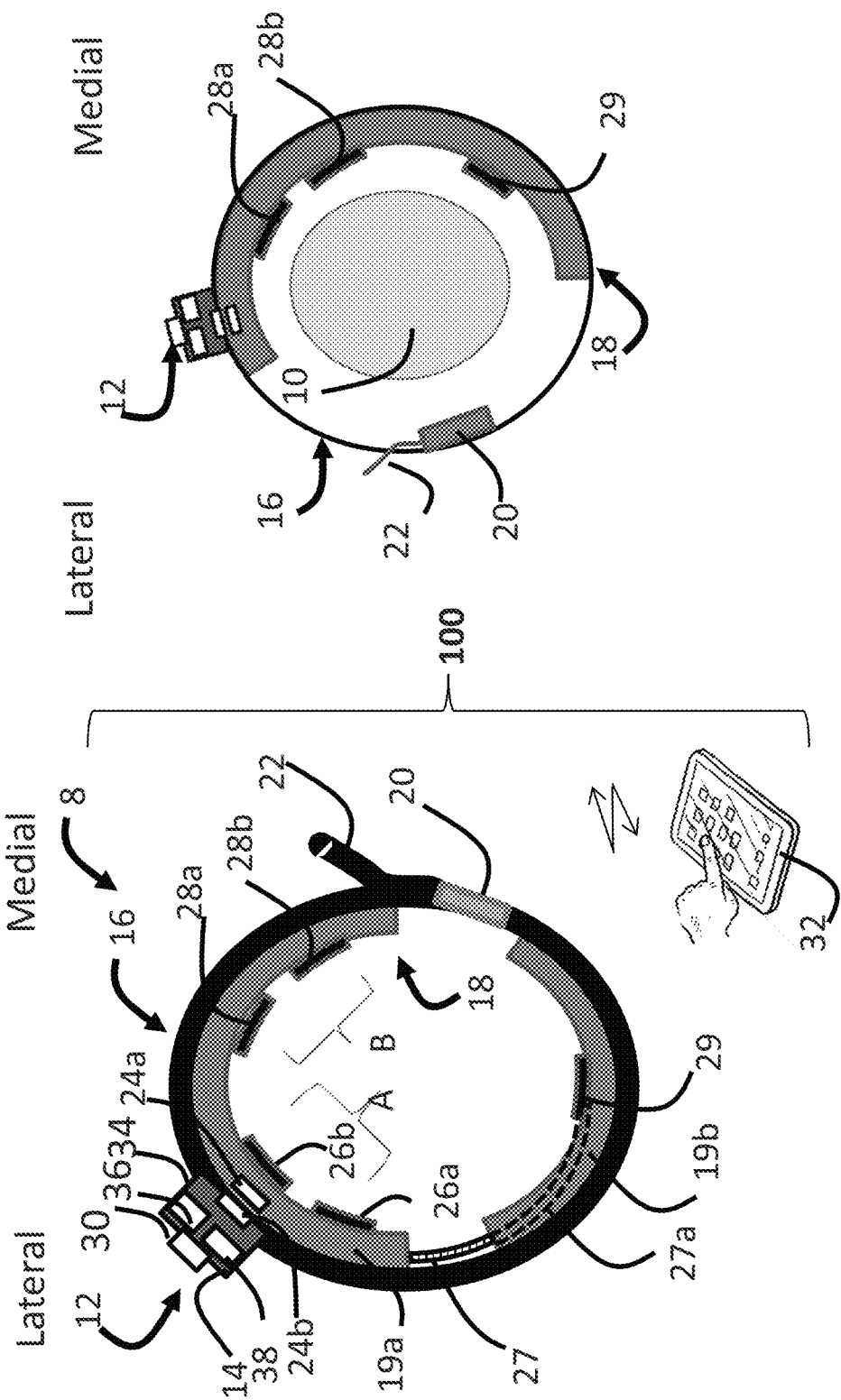
FIGS. 1A-1B are schematic views showing novel TENS systems.

FIG. 1A shows a system 8 realized in a preferred embodiment of the invention. The system may be implemented as four components including a therapy device 12, a band 16, an electrode array 18 having at least 2 electrodes, and a user device 32.

The therapy device 12 is realized within in a single housing 14 (as shown) or is distributed into electrically connected components each housed independently (and flexibly connected) which provide the electronics and other hardware, software, and power used by the system 8. In an embodiment the system 8 is realized as a TENS system and its components allow conformation to a portion of the anatomy of a user's leg 11, such as the knee, upper calf, and/or ankle area. The system can also, or alternatively, be designed to provide peripheral nerve stimulation for treatment of medical disorders and designed to be used, for example, on an individual's arm, upper leg, head, back, pelvic area, or internally, such as within vaginal or anal areas, or elsewhere. The stimulation protocol and/or electrodes can be selectively configured to treat at least one disorder or unwanted state related to pain, overactive bladder (OAB), migraine, headache, tremor, blood pressure outside a target range, cardiac disorders, sleep, pelvic disorders, immune disorders, brain disorders. Alternatively, treatment may be provided to improve brain activity relate to cognition, attention, and learning, or to treat addictions, drug abuse, etc. Stimulation may modulate biological, physiological, immunological, and metabolic states and conditions.

The device 12 contains at least one stimulus generator with associated signal conditioning circuitry (e.g., D/A, routing, multiplexing, and amplification hardware) for providing stimulation signals during therapy. The device 12 also includes power module 59 having a power source such as a rechargeable battery and/or wireless energy harvesting circuitry, and a control module 40 to control stimulation. The control module 40 includes or communicates with controls and hardware of a user interface 30 which is part of a user interface module 44 that allows a user to control the device operation. The circumference of the band 16 is adjustable to the user's limb by a securing element 20 such as a buckle or hook and loop fastener. This allows the circumference of the band 16 to be tightened by pulling on the tip 22 of the band.

The electrode array 18 comprises a set of one or more electrical contacts having a first connector port 24a that is configured to be reversibly coupled with (e.g., "snapped onto") a second connector port 24b provided on the housing 14 of the device 12 in order to electrically communicate signals between the device 12 and the array 18 and to mechanically and electrically connect these two components of the system 8.

Alternatively, when the system 8 is realized in a distributed manner the connector ports, 24a, 24b are connected by a conduit having at least two electrical paths provided therein to create a stimulation circuit. Preferably, connection ports 24a, 24b are realized with multiple contacts that allows discrete routing to individual TENS electrode contacts. Dynamic routing of signals to selected electrodes occurs using routing circuitry and/or electrical switch circuitry under control of the therapy device 12 or a user device 32. The device 12 or user device 32 communicates with other components of the system 8, in a wired or wireless manner, to control routing of stimulation signals to selected electrode stimulators of the system such as 26a/b, 28a/b, and 29 according to a stimulation protocol. Direct electro-mechanical connection between the device 12 and one or more of the electrode contacts eliminates the need for, or reduces the number of, conventional lead wires that are relied upon in comparison to most conventional TENS system designs. In addition to a direct electromechanical connection to electrodes, or to an electrode array, some embodiments use one or more conventional lead wires to communicate stimulation signals from the device 12 to electrode contacts. In embodiments, both lead wires and a fixed electrode array are used to allow for flexibility in the shaping of the stimulation field.

In embodiments, the device 12 provides power, data, and communication connectivity with other devices using either wireless transfer or a communication port 34 (e.g. a USB port). The port 34 interfaces with the communication module 52 configured to allow for data upload (e.g., stimulation protocol values) or download (e.g., a historical record of device operation to assess compliance). For example, a user selects a stimulation protocol on a user device 32, such as a laptop, and then connect a cable to the port 34 to upload the protocol to the device 12. The therapy device 12 is configured to withhold stimulation, or otherwise provide safety isolation, if the port 34 is connected. System designs and methods for provision of patient safety and isolation are well known. One method is to cause the control module 40 to "break" the circuit that normally connects the connection port to the electrical waveform generator of the stimulation module.

In embodiments, the device 12 utilizes a first pair of electrode contacts 26a, 26b ("labeled A" in the figure) that is configured to stimulate a first anatomical region. For example, electrode contacts 26a, 26b provide stimulation to the lateral side of the leg (e.g. upper shin area) over a portion of the sural nerve to stimulate the patient in the treatment of pain. A second pair of electrodes 28a, 28b are positioned to provide stimulation of the saphenous nerve on the medial aspect of the leg (labeled "B"). The provision of a first and second pair of electrodes, operated in accordance with selectable stimulation protocols, can allow for the same device to provide selective treatment for pain, overactive bladder, or both.

In an embodiment the device 12 is configured to provide a first stimulation protocol for treatment of pain to the first pair of electrodes "A", and the stimulation protocol parameters are set for pain treatment. For example, a pain treatment protocol uses a frequency, or set of frequencies selected between approximately 60 and 100 Hz. The device 12 is also, or alternatively, configured to provide a second protocol for treatment of OAB and stimulation occurs using a frequency, or set of frequencies, selected between approximately 2 and 50 Hz and second pair of electrodes "B". A range of between 5 and 20 Hz may be preferred for OAB treatment. In an embodiment, the system allows selection between two or more treatment protocols depending upon the symptoms for which relief is sought. A user can control the therapy that is provided in a selectable or programmable manner. In an embodiment, stimulation of lower leg nerves, is also used to improve sleep in individuals who do not suffer from pain or overactive bladder such as insomniacs or healthy individuals. In the case of the saphenous nerve (SAFN), the stimulation may occur at 10 or 20 Hz. The inventors have shown that stimulation of the SAFN of at least 30 minutes and twice a week decreases frequency of night-time voiding. While this may be caused by decreasing bladder over activity, it may also be due to promoting normal sleep.

In an embodiment, the device 12 is configured to utilize a first electrode array positioned to stimulate the lateral portion of the leg "A", and/or a second electrode array is positioned to stimulate the medial portion of the leg "B". A first array containing first pair "A" has a first inter-electrode spacing, orientation, and geometry configured for treatment of pain. A second array containing electrode pair "B" has a different position and configuration, and is provided for treatment of a pelvic floor disorder such as OAB. The first and second electrode arrays can have different electrode sizes, geometries, orientations and inter-electrode distances. In an embodiment, two electrodes or an array, and at least one port 24a should be configured so that the device 12 resides in (or on) the band 16 and is positioned to deter the device 12 from rubbing against the inner leg of an individual who is walking or sleeping.

In an embodiment, the electrode array provided during treatment of pain is disposed approximately circumferentially (i.e. the electrode pads are positioned along a horizontal axis), and the array used for treatment of OAB is oriented vertically or at least has vertically offset pads. Using vertical offset (i.e. longitudinal to the axis of the limb) and adjusting the distance between the two electrodes may provide greater recruitment of SAFN fibers. For example, separating adjacent edges of the electrode pads by at least 2 to 4 inches may allow for a sufficient depth of the stimulation path. However, this may not be possible or may result in unintended stimulation of non-target nerves (or muscle) with horizontally oriented arrays, especially as configured for use with a limb.

In an alternative embodiment, an additional electrode contact 29 is provided using a second segment 19b of an electrode array. The second segment is electrically connected to the first segment 19a by a conduit 27 (e.g., a multi-stranded wire) which runs from the port 24a to each of the electrodes of the array 18. A portion 27a of the conduit 27 that resides within, or is attached to, the electrode array 18, is shown as a dashed line in FIG. 1A. While array 18 is shown as relatively thick compared to the band, it may be realized as a thin rectangular pad, with electrode contacts positioned on its surface. In an embodiment, the array 18 is formed upon a pad that has foam backing in order to increase patient comfort. The second segment allows for flexibility in the electrode spacing.

FIG. 1B shows an alternative embodiment wherein the band is wrapped around a user's leg 10 and is configured and sized such that a pair of electrode contacts 28a, 28b are located to stimulate the anteromedial aspect of the leg just below the knee. There is an electrode 29 configured for position on the posterior or posterior-medial leg region. Electrode 29 is spaced further away from electrodes 28a, 28b, and may be located more cephalad on the array. Electrode 29 may be used by a stimulation protocol (in conjunction with either electrode 28a or 28b) to provide a larger stimulation field that is provided compared to when only 28a or 28b are used. In some users, this electrode can provide stimulation of the tibial nerve that travels behind the knee.

As will be disclosed, in embodiments, electrodes 28a, 28b and 29 are realized within an array design that permits adjustable electrode pad locations. For example, the array may be realized using a "track" which can allow electrodes to be "snapped" or "slide" into different positions by a user. Alternatively, users or doctors can assess one or more areas on the leg. This information can then be used to select pre-formed electrode array designs having selected distances (e.g. to accommodate different shaped legs or different SAFN locations). The distance that is appropriate between electrodes is related to the distance required to provide stimulation in an effective manner for an individual patient. For example, if three electrode distances are used by three different electrode array model sizes, then the patient or doctor will determine which pre-formed or adjusted electrode array is correct. Assessment includes stimulating the patient's leg at different locations and selecting the electrode array that is associated with the regions that produced the most intense sensory response or had the lowest stimulation sensory threshold. As will be disclosed, assessment of positioning and parameters for stimulators (external or internal) may include using other relevant criterion or measurement.

In an embodiment, the device 12 includes a user interface module 44 which is operated by at least one control on the device housing 14 such as a button that the user operates for halting/pausing/starting therapy. One or more additional buttons may also be included for allowing control of stimulation amplitude, or other functionality. Patient signaling is provided by a visual indictor 36, which may include an LCD or LED (which can change color, blink, etc) to indicate various aspects of the stimulation therapy or state of the system 8. The user interface module 44 provides other signaling components 38 which allow for multi-modal signaling such as a speaker or vibrotactile stimulator realized using a small vibrator 39 (see FIG. 3B) such as an electric motor used in many cellphones. In addition to text or graphic patient notification, patterned stimulation using light, sound, or vibration can provide signaling. For example, a patient is notified that there are only 5 minutes left in a treatment session by a pattern of, for example, three 2-second pulse trains separated by 1 second periods of silence.

The systems shown in FIGS. 1A and 1B can be used to treat many disorders. When applied to the lower leg, at the level of the knee (e.g., just below the "patella"), TENS can be used to treat disorders such as OAB, stress, urge, and mixed incontinence, and other pelvic floor disorders and their associated symptoms. Other unwanted states or disorders such as pain can also be treated.

For treatment of pain or muscle stimulation the electrodes may be applied at candidate stimulation locations by an individual user or doctor until symptom relief is obtained or until a behavioral, sensory, motor, or physiological response is produced within hours of therapy provision. For OAB, the symptom relief may take longer (multiple days, weeks or months). In this treatment, other methods may be used to confirm appropriate stimulation.

Recently the Inventors have discovered that SAFN stimulation is able modulate bladder function and can be used in order to treat patients with OAB. Current electrical treatment of overactive bladder is done using PENS (with a needle electrode), or more invasive implantable devices, to stimulate the sacral or PTN. A TENS unit designed to stimulate the SAFN may be realized using a circumferential stimulation system as disclosed herein. A circumferential TENS system can provide a number of unique advantages when certain features/characteristics are incorporated into the design. For example, the sural nerve fibers which are being targeted for pain treatment by prior art stimulators are modulated at approximately the 60 to 100 Hz range. In contrast, stimulation of the SAFN should occur in the approximately 1 to 50 Hz range, preferably at around 20 Hz, or oscillating between 5 and 20 Hz, or 10 and 20 Hz. Additionally, the electrodes should be positioned to stimulate the SAFN branches. In addition to one or more electrodes that may be realized on an array disposed within a circumferential ring that is realized at a single annular position along the leg, it may be preferable to provide electrode locations that are vertically offset to increase the stimulation field and SAFN fiber recruitment.

Figure 2:
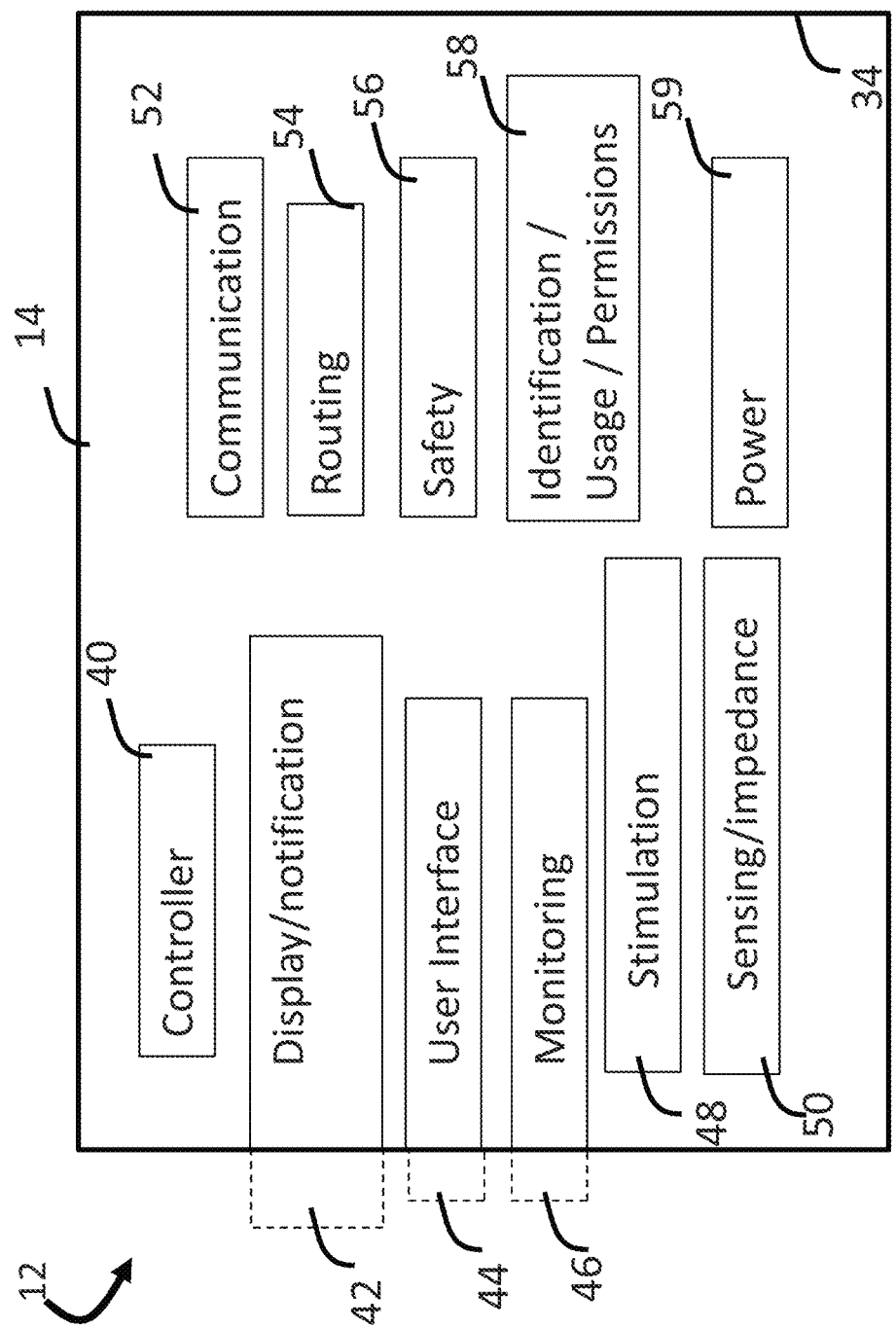
FIG. 2 is a schematic view showing components of a TENS apparatus such as that shown in FIG. 1A.

FIG. 2 shows an embodiment of the wearable device 12 with modules (software+hardware) that provide the different features of system 8. Modules 42, 44, and 46 are shown as partially dashed lines that extend outside of the housing 14 to indicate that some components of the module (e.g., buttons, displays, transducer, speaker, etc.) extend outside of the housing, or reside on the housing and connect to circuitry located inside the housing. A similar stimulation device 12, which can be used to realize some of systems and methods disclosed here, was disclosed in US Pub. 20170361093, to Yoo and John, fully incorporated by reference herein. Any module disclosed in the device 12 can be realized in a different component of the system 8.

In an embodiment, elements of the user interface 44 (e.g., push button and LEDs) are physically located on device 12 housing 14. In alternative preferred embodiments, one or more user interface components may be realized on a separate user device 32. The operation of separate/remote user interface elements of the user device 32 may be communicated with the device 12 through a variety of means including a physical link such as a wire, a wireless link (e.g., WIFI or Bluetooth), an optical link such as an infra-red (IR) connection, etc. When the user interface elements are remotely located on a dedicated user device 32 this may be a custom remote control specifically designed to control device 12, or the functionality may be incorporated into generic devices used by the patient such as a smart phone or tablet computer.

A control module 40 controls the other modules of the device 12, and allows for the provision of therapy according to parameter settings of a therapy protocol. The display/notification module 42 includes visual displays and associated circuitry for presenting information. Notifications can also be presented in other sensory modalities such as sonically or tactilely. The user interface module 44, provides at least one user control for allowing adjustment of therapy (e.g. turning therapy on/off or increasing/decreasing stimulation intensity), and can have a microphone 84 for accepting voice commands. The monitoring module 46, monitors information related to the patient or the device from various sensors or provided by patient input. For example, information about the orientation of the device or activity of the patient can be monitored. Impedance data obtained by the sensing/impedance module 50 can be evaluated by the monitoring module 46 and cause the stimulation to stop, or a patient to be issued a notification, if the impedance drops below a minimum defined threshold. The inter-electrode spacing should usually be sufficient to deter shorting (e.g. at least 1 inch). The distance may be decreased in certain configurations, which may increase this risk. The device 12 may be configured to detect when two electrode pads contact so that the gels of two oppositely charged electrode pads are shorted together. Responsive stimulation may be provided by the system in a closed loop manner, using algorithms, rules or control laws.

The stimulation module 48 has a stimulus generator and provides stimulation waveforms according to the stimulation protocol of the treatment protocol, and can work with the routing module 54 to provide stimulation signals using various combinations of electrodes (or other stimulators) at different moments in time. The safety module 56 provides features and routines related to patient safety, such as providing for electrical isolation of the stimulation module 48 from charging circuitry, and batteries (if included) of the power module 59. The communication module 52 allows for communication between different components of the system 8, and between the system and external devices or remote computers such as computers at a doctor clinic. The identification/usage/permissions module 58 can enable system components to be identified (e.g. the serial number of an electrode array, a ID of a user's cellphone), usage measured, and permissions granted or denied, for example only a doctor may be allowed permission to increase the maximum amplitude of stimulation or the amount of stimulation provided within a specified amount of time. The usage data may also be reviewed or assessed in relation to patient compliance. Compliance can be assessed in relation to treatment goals such as minimum % of weeks where the patient provided stimulation at least for a minimum defined number of treatment sessions per week or total treatment per week.

Usage data may also relate to the number of hours or stimulation sessions for which a set of electrodes, or an electrode array, have been used. An electrode array 18 can be used multiple times and may allow for about 2 weeks of stimulation, when used daily, to be provided before requiring replacement. Some users may wish to attempt to extend the life of an electrode array rather than obtaining a replacement as suggested by a manufacturer in order to decrease cost of using the system. Alternatively a user may simply forget to replace the electrode array as suggested. This type of user non-compliance may increase risks such as damage to the conduits of the array, or decrease in adhesion of the electrodes due oil or dirt from a user's skin, so that stimulation does not occur as intended. Other problems with re-using the array are related to risk of electrical shock or electrode shorting, mis-calibration of the device with respect to settings that were previously successful and decreased efficacy due to less energy being provided to the patient over time. In an embodiment, usage data may be operated upon by the monitoring module 46 to provide alerts to a user, doctor, distributor, or other third party by modules 42 or 52 to indicate that a battery or electrodes should be replaced. In an embodiment, after a certain number of uses, or duration of use, which is recorded by the device 12, the system is programmed to automatically contact a company or distributor (e.g., CVS.com) over the internet via the communication module 52 to automatically ship replacement parts (e.g., TENS arrays or tens pads) to a user. The usage/permissions module of the 58 system may be designed to halt further stimulation until the order is placed via a shopping cart application. In an embodiment, an electrode array may contain a memory chip, RFID, or circuitry for providing a unique ID to the device 12 so that the device can measure the total duration and\or number of times that an electrode array has been used. The device 12 can communicate with software operated in the user device 32 which allows the operator to use 'one click' purchasing of replacement device parts from within the device 12 "app".

In an embodiment, device operations are logged in device memory (e.g. in the control module 40) or memory of an external controller 32. Such data logging operations can include data related to for example, times when stimulation was started and stopped as well as what stimulation parameters were used. Sensed data obtained from the sensing module 50 can also be logged. The device log information can be displayed by the user interface module 44 on the LCD in summarized or tabular formats and also can be communicated in a wired or wireless manner between any system components including implanted devices, external devices, and remote devices such as a computer at a clinic or manufacturer of the device. When an external device 32 is used to control the system 8 and to allow user input commands to the system for any other reason, then the external device 32 may perform the logging operations either independently or in combination with the control module 40 of the device 12. When the device 12 is operated independently from, and without interaction with the external device 32, then during therapy the device 12 can be powered on either from a low power stand-by state or from an off-state. However, either state should allow for information to be stored and maintained by the device 12 for later review and/or retrieval.

In an embodiment, the device is designed so the monitoring module 46 causes stimulation treatment to be intermittently paused while impedance is assessed to insure treatment is provided as intended. The impedance can be tested at the beginning of each therapy session, or can be tested intermittently, such as every minute, or every 5 to 10 minutes, during the provision of therapy. If the impedance is not above a minimum criterion the user can be alerted. In an embodiment, if too many impedance values occur above a specified limit value across a selected use-period or number of uses (i.e. any day when the device is used), then the user may be prompted to replace the electrode array. For example, if during 3 out of the last 5 the impedance rose above a threshold during use, then replacement is merited.

In an embodiment, the device 12 can be voice controlled as provided by the user interface module 44. For example, a user can depress a button on the device and say "increase 2" in order to increase the amplitude of the stimulation signal by 2 units. After the adjustment, the device can listen during a defined interval such as 5-10 seconds so that a user may provide an additional voice command such as "increase 3". A limitation can be put on how many times the device can be increased within an interval. For example, a command to "increase 3" may be rejected after this has occurred twice if the amplitude is already above a typical comfort level used by a patient. This type of restriction may also be imposed upon changes in stimulation intensity that are attempted manually by a patient to deter unwanted or unintentional adjustments. For example, a graphical user interface provided on a smartphone which allows a user to increase stimulation amplitude may require confirmation if stimulation above a certain level is selected by a user. In this case a notification such as "are you sure you want to increase stimulation amplitude to X?" message may appear and require a user to select "yes" instead of "no".

Additionally, in an embodiment the device monitoring module requires user confirmation of a voice command to deter unauthorized adjustment of stimulation. For example, if a user instructs the unit by saying "increase 3" the system may then prompt the user for confirmation such as "Do you want to increase stimulation by 3 levels?" and the user must respond "yes" before the change occurs. The verbal instructions can incorporate interaction with a cellphone app that is used to adjust device operation. The voice control capability may require a password or voice recognition of a user so that third parties are not able to provide voice control commands. Voice control may be implemented using a natural voice service such as Alexa Voice Service that is configured to communicate with the communication module 52 of the system. The communication module may store parameters that are used to restrict voice commands to those provided by the user or caretaker (i.e. voice recognition can be restricted to a particular user). Similarly, manual adjustment of parameters may require finger-print or password authorization.

In an embodiment, the device 12 is configured to operate interactively with a user in order to define stimulation parameter settings which are assigned qualitative meanings such as "threshold", "comfortable", "strong", "very strong" and "uncomfortable". For example, a user can press buttons to indicate these attributes during a calibration routine where the intensity of stimuli are adjusted. A user can then simply select "very strong" rather than having to increase or decrease stimulation settings to cause the stimulation module 48 to provide a particular level of stimulation. The stimulation settings can also be set differently for states or activities such as "sleeping" or "walking". These may be lower or higher than those preferred when the user is simply sitting in a chair and receiving stimulation treatment. As discussed, the device can monitor and detect these two states using sensed data such as accelerometer data, and/or time information.

Multimodal Sensing and Stimulation

In a preferred embodiment the system 8 includes a position, motion, and/or muscle activity sensor as part of the monitoring module 46 (e.g., an accelerometer and/or level detector), to detect movement, posture, and/or changes in patient position. A three-axis (x, y, z) accelerometer, such as may be realized using a semiconductor chip, is used to measure the device or band orientation due to the effect of static gravity on each axis (i.e., x, y, z) as well as acceleration due to user motion along one or more axes. A gyroscope sensor is provided to measure rotation. The module 46 also has an electromyogram (EMG) sensor which is realized as a microphone or electrode and circuit that can measure muscle activity.

In embodiments, the module 46 is configured to record the mechanomyogram (MMG). This is the mechanical signal measured from the surface of a muscle during contraction variants such as acoustic myography (AMG), using devices such as microphones and contact transducers (e.g., piezo-electric devices, strain gauge). At muscle contraction onset relatively large changes in the muscle shape can cause peaks in the MMG. As the movement progresses subsequent vibrations can be measured due to oscillations of the muscle fibers. For example, band pass filtering the MMG and integrating amplitude or area under the curve (rectified) over time can be used to detect movement or changes in movement. The mechanomyogram can also be referred to as a phonomyogram, acoustic myogram, sound myogram, vibromyogram or "muscle sound". The MMG or AMG may have advantages over measuring EMG in that it can be measured at the same time as stimulation without interfering with the electrical path of current through issue or electrical artifact due to stimulation.

Pressure sensors can be embedded on the device housing 14, in the band 16, or adjacent to the surface electrodes of an array 18 to measure the contact pressure between the stimulating surface and the skin. This pressure signal alone, or in conjunction with MMG/AMG data, can be used to increase/decrease the stimulation parameters, completely halt the stimulator, or provide an alert signal to the user to indicate a potential problem such as a loose band. This combination of feedback-controlled stimulation can allow patients to receive therapy while performing most daily tasks.

The sensed muscle activity can be used to detect several types of muscle activity that are relevant to treatment with nerve stimulation. In an embodiment, a muscle response in the foot can be detected and this detection can be presented to a user using a visual or auditory signal to confirm successful nerve recruitment. For example, a sonic signal may be derived from measuring a feature of the MMG and can be presented to a user to indicate that PTN stimulation has produced a motor response in the foot. This may be helpful to a doctor user who is unsure if the amplitude of the stimulation has been increased to a sufficient level to produce a clinical response when the invention is used to provide stimulation of this nerve target.

Additionally, an advantage may be provided by sensing and evaluating movement or position data. These data can be assessed by the monitoring module 46 and used to weaken/halt stimulation. For example, stimulating the PTN may change the muscle tone near the ankle and/or foot. Accordingly, providing PTN stimulation while a patient is walking (or even standing) may increase the risk of the patient tripping or falling. Further, providing stimulation that affects motor/muscle activity near the posterior tibial nerve, foot, or lower leg can increase the risk of muscle tear and damage. For example, if a muscle group does not operate during walking in the same manner that it does in the absence of stimulation, then it may cause other muscle groups to compensate. Since nerve stimulation may increase the risk of adjacent muscle "tearing" or related damage, the system 8 can be configured so that it stops or pauses stimulation during certain defined conditions associated with walking or standing. Rather than pausing or reducing stimulation, the system 8 can operate the display/notification module 42 to provide an alerting signal to indicate the user should consider halting or pausing the stimulation due to sensed movement/position information meeting a selected criterion.

The system 8 can also be configured to recognize a "stimulation resume" condition that may be defined in various manners so that stimulation is not weakened/halted longer than intended. For example, after a certain amount of time has elapsed, or sensed data indicates that a user's leg is again in a horizontal position, or sensed data indicates that muscle activity has remained below a selected amount for a selected duration, then the device 12 may resume stimulation. Alternatively, the system 8 can alert the user to remind the user to restart the stimulation. The treatment criteria used to modify stimulation to reduce the risk of harm to the patient can be modified based upon such factors as whether the treatment is provided during a time when the patient is expected to be asleep or awake. For example, when the stimulation occurs during a time when the patient is expected to be sleeping, then a simple change from the horizontal to vertical position may be sufficient to cause the system to weaken/pause stimulation. The system will then modify stimulation until sensed data indicates that the device 12 has returned to a horizontal position for a period such as 5 minutes. Accordingly, in the case of a user who awakens in the night to go to the bathroom, or for another reason, upon putting their feet on the floor (e.g., the orientation of the wearable device transitions from horizontal to vertical) the system 12 will weaken/shut off stimulation. This stimulation will not resume until the user has returned to their bed and lies down again for at least 5 minutes. The parameters that define the time when a patient is typically sleeping can be adjusted by a user relatively easy during the initial programming of the device, the device may algorithmically learn this over time. Additionally, a user may indicate that he/she is going to sleep for the night simply by pressing a button on the device 12, or in other various well-known manners such as pressing a virtual button on an "app" operated in the user's smartphone.

In an embodiment, the monitoring module 46 may be configured so that stimulating will still continue if the leg is upright, but will weaken/pause if motion or muscle activity over a certain amount is also sensed. This is an advantage for users who may not provide therapy stimulation with their leg in a horizontal position. Additionally, the monitoring module 46 may be configured so that a "pause" criterion is defined only during certain hours.

For example, if the device detects a change in position from horizontal (e.g. 0 to 45 degrees) to vertical (60-90 degrees) between 10 p.m. and 7 a.m. then the device may simply pause, or may issue a sonic alert, because this may be associated with a user who is getting ready to stand up out of bed. Stimulating during this time may present an increased risk of falling or muscle damage when a patient starts walking after having slept. While this concern may be higher when stimulation is applied to the lower leg near the foot, for example, during PTN stimulation, this strategy may be applied to other target stimulation areas or treatment of other disorders as well. Instead of a TENS, the system 8 can be designed to provide wireless energy to an implanted device using either electrical, RF, magnetic, microwave, or other type of energy. In this case, the monitoring module 46 can be used to modulate the transmission of energy or commands to adjust operation of the implantable device and decrease risk of harm. When the device is fully implanted with sensors, then the device may be designed to operate similarly.

The above features and necessary hardware (e.g., sensor) can be realized in an implanted neurostimulator or within an external controller that is attached to a patient's body or leg. Rather than using electrodes the wearable stimulator can be configured with a stimulation module 48 that contains coils or other transmitter that controls the implanted device 89 operation. The motion/position sensor can allow the monitoring module 46 to assess sensed data and identify changes in patient orientation and activity, such as lying, standing, walking, etc. to track activity. This can both permit modification of the stimulation characteristics according to the sensed motion/position data and can also keep track of patient activity. For example, in the assessment of OAB disorder, the system 8 tracks the number of times an individual stood up during the night for at least a certain amount of time. These data can be used to infer how many times the patient went to the bathroom during the night. Presenting this data to a patient upon waking may increase the accuracy of recall for patients who do not typically remember this activity in the morning. Additionally, in the morning at a selected time such as 8:30 a.m. the system 8 can provide a prompt to the user to verify whether a certain number of bathroom trips occurred. This type of verification is valuable since not every "trip" will be one made to the toilet. In an embodiment, at 8:30 a.m. the system 8 evaluates the sensed activity to calculate the total times a patient stood up (or uses other criteria for candidate bathroom trips) during the preceding 8 hours. The user is then prompted by an auditory alarm to answer a question which may be presented by their cellphone "Did you go to the bathroom 3 times last night". The user can press a button "yes" (or say yes if the software running on the user device 32 is configured for voice recognition). Alternatively, the user may select "no" and then provide the number of bathroom trips. If the user does not respond then the candidate bathroom trips are either stored as non-confirmed in device memory or are deleted.

Alternatively, a transmitter may be located near a user's toilet. The transmitter is configured to wirelessly communicate with other system components to automatically log each time that user entered the bathroom. Additionally, a duration such as the length of time spent within a distance such as 2 feet from the sensor (near the toilet) may also be recorded.

In an embodiment, the system 8 tracks phenomena such as the number of leg twitches which occurred during the night and assesses (and tracks over time) measures such as restless leg syndrome. The treatment of conditions such as OAB may cause the patient to have a more restful sleep as reflected by less bathroom trips and a decrease in restless leg syndrome. The system 8 may also use leg movement, or other accelerometer-derived measures, to adjust, temporarily pause, halt, increase or decrease stimulation to avoid interfering with sleep.

In an embodiment, the monitoring module 46 is programmed so that accelerometer data (or other sensed data) are collected and stored throughout the night in order to determine measures related to overall sleep quality, leg activity measures, and trips to the bathroom, even if stimulation is only provided for 30 or 60 minutes, or not provided.

In an embodiment, the detection of muscle response evoked by stimulation is used to provide screening of a patient, location of electrode placement, or stimulation parameters for example, when assessing PTN stimulation. If stimulation evokes a muscle response that meets a selected threshold then the site and stimulation parameters is assessed as successful, whereas lack of the muscle response indicates that either the site or the stimulation parameters should be changed. If multiple sites and stimulation parameters fail to evoke a muscle response defined in a screening criterion, the stimulation may not be a suitable treatment for the patient.

In embodiments, the system 8 includes one or more haptic stimulators such as a vibrating motor 39. Haptic stimulation may be used to mask or otherwise decrease unwanted sensations related to electrical stimulation. Additionally, various tactile and vibrotactile stimulators can be used to adjust stimulation sites and parameters by providing sensory stimulation (e.g. pressure or pain) which may be used to assess the effects of electrical stimulation. For example, if stimulation is successfully modulating nerve activity (e.g. sural or SAFN stimulation), then the sensation provided by a haptic stimulator located distal to the site of stimulation, may be masked or decreased. This indicates that the device is stimulating a nerve effectively. This may be an important feature in patients who fail to detect the nerve stimulation in a manner typically associated with successful nerve recruitment. For example, even if a patient does not subjectively assess SAFN stimulation as producing a radiating sensation distal from a region of stimulation, if the electrical stimulation serves to decrease vibrotactile sensation experienced by a patient (i.e., mask the transmission of sensory information) then this may indicate a patient is receiving sufficient modulation of the SAFN. Successful nerve recruitment may also be reflected by an increase in the electrical stimulation level related to either sensation or discomfort/pain threshold.

In embodiments, the haptic stimulator may be connected to the band 16, or may be located caudal or distal to the band 16. At least one vibrating element 39 may be connected to a secondary band that is attached elsewhere on the leg to provide vibratory stimulation in that region. The vibrator 39 may be attached to, or formed using, smooth, textured, or pointy surfaces which excite nerves that sense pressure or pain.

In summary a vibration can be used to mask stimulation or confirm nerve recruitment. It can help during assessment of stimulation protocol and electrode position. In the former, if the vibration occurs more proximally to the site of electrical stimulation then vibration can mask an unwanted sensation associated with the provision of electrical therapy. In the latter, when stimulation is used to recruit a target nerve, then a sensation of vibration more distal to the site of stimulation should decrease when the nerve is being stimulated effectively.

Wearable System Designs

Different embodiments of the system 8 have unique advantages as will now be reviewed in FIGS. 3A to 3F. Rather than a single band, these figures illustrate system embodiments which use more complicated designs and stimulation schemas.

Although the system 8 may be shown as worn on the patient's upper calf region 61, an embodiment using a single band having a horizontal electrode array may not be suitable for some treatments and may suffer disadvantages. For example, a horizontal stimulation field may not provide sufficient, or any, SAFN stimulation. Additionally, in the treatment of pain, an individual's pain may not be relieved, or sufficiently relieved, using a TENS system 8 with a single band configured to stimulate the sural nerve. While amplitude and other stimulation parameters may be adjusted to enable greater nerve recruitment and pain relief, target nerve recruitment may be greatly affected by the electrical path between two or more electrodes as realized on a semicircumferential or fully circumferential geometry. Further, using an electrode which stimulates the sural nerve on the lateral surface of the leg, and another electrode which stimulates the SAFN on the medial surface of the leg may cause the stimulation to be limited because the activation of the sural nerve may cause discomfort at a lower amplitude than that which is tolerable for the SAFN, or vice-versa.

It may advantageous that if the treatment is for OAB and the target is the SAFN then only the medial aspect should be stimulated while if the target is the sural nerve and the treatment is for pain, then only the lateral aspect should be stimulated. Using vertically offset or oriented electrode arrays can provide this potential advantage.

Typically, when electrodes are closer, the path between these can become shallower and activate a smaller crosssection of tissue. Accordingly, providing at least one electrode displaced vertically and on the medial aspect of the leg may increase the ability of the system to modulate nerve activity. This can be true for treatment of pain and for the treatment of OAB. Two closely spaced electrodes may not provide sufficient recruitment compared to electrodes spaced further apart. In illustrated embodiments, two or more vertically offset electrodes may be realized within a first electrode array or in combination with a second electrode or electrode array.

In some users, vertical rather than, or in addition to, horizontal displacement of the electrodes may be the difference between successful and unsuccessful treatment. When stimulating the saphenous or sural nerve, improved performance (recruiting a larger number of nerve fibers) may occur with an electrode pair that has a vertical gap of at least approximately 1.5 inches, and preferably 2.0, 2.5 or 3 inches to provide sufficient recruitment of neural tissue. The electrode array may be vertically offset, or both vertically offset and circumferentially distributed, rather than simply being implemented in a circumferential arrangement.

FIG. 3A shows an embodiment with a first band 60*a* that secures a TENS device 64*a* to the patient's leg 10. This may reside in an upper calf region 61 that is bounded on the distal end slightly (e.g. 1-2 inches) below the medial head of the gastrocnemius and extend up to the level of the patella. Most typically the upper side of the band 60*a* will be attached in an area about an inch or two below the patella. A second band 60*b* is shown situated near the bottom of the gastrocnemius muscle but may also be placed above (or below) this level to deter unwanted stimulation of the calf muscle. Typically at least one electrode pad stimulator is provided for each band and positioned between the medial and anterior aspect of the leg. The position of electrodes should deter/minimize stimulation of calf muscle and selectively stimulate the SAFN.

In an embodiment, the system is configured so that the device 64*a* provides stimulation which travels between at least one electrode pad on the upper band 60*a* and one on the lower band 60*b*. For example, the upper band provides stimulation using an electrode array having at least two electrodes, and the lower band uses either a single electrode contact or also utilizes an array. Both the upper and lower bands may each use only 1 electrode rather than an array of 2 or more electrodes. A connector conduit 62 communicates electrical signals between the first and second band. The conduit 62 may be electrically attached to a port 34 on the device 64*a*, a port 98 (see FIG. 5) on electrode array 18 of the first band, or a port provided on the band 18 itself which is, in turn, electrically connected to the array or device 12. Using 2 bands and a flexible conduit can provide greater flexibility to different shaped legs compared to using a single band.

Although the TENS device 64*a* can be positioned on the anterior-medial portion of the leg to stimulate the SAFN, this may be less comfortable than other embodiments. For example, using a band and array design so that the stimulator is positioned anteriorly (approximately midway between the lateral and medial portions of the leg) may be most easily accessible by a user. Also, if the system is used during sleep positioning the device medially may cause discomfort or pressure that is experienced on a portion of the patient's inner leg. Accordingly, in embodiments the device 64*a* and band 60*a* are configured to enable device positioning on the anterior, posterior, or lateral aspect of the leg, rather than medially, while still permitting a) the array to be positioned to stimulate the SAFN, and b) connection of the conduit 62 so that at least one electrode or array of the lower band 60*b* is positioned correctly (i.e. preferably medially rather than laterally on the leg when treatment of a pelvic floor disorder is provided).

In an embodiment, during an initial use of the system 8 a user connects an electrode array 14 into stimulator 12 (FIG. 1B) to realize a mechanical and electrical connection between the two system components. Using band 16, the combined assembly is then attached onto the upper calf region so that the pads of electrode array 14 are attached to and biased against the skin of the user. An advantage of using a band to secure the assembly to the patient is that the electrode array may last longer compared to a design in which electrodes were simply stuck to a patient and the connection relied only on the adhesive properties of the electrode gel. The use of a band can serve to secure the array to the patient and extend the functional life (number of uses) of the electrodes, even though the adhesiveness may decrease over time.

FIG. 3A also shows an alternative embodiment in which a third band 60*a*' which houses device 64*a*', is connected to the second band 60*b* using conduit 62'. This configuration allows for stimulation of both the SAFN and the PTN when at least one electrode on the third band is located posteriorly. In an embodiment, the electrode of the second band is located anteriorly between the medial ridge of the tibia and the border of the calf muscle. The third band may be used instead of the first band 60*a*, device 64*a*, and conduit 62. Additionally, if the third band uses an electrode on the medial anterior portion and an electrode on the medial posterior portion then both the PTN and the SAFN may be stimulated, without requiring a first or second band since the SAFN has an anterior branch. When the SAFN is stimulated in the upper calf area users may feel a tingling sensation that spreads down the leg to the level of the ankle and even further into the arch of the foot. During stimulation of the SAFN near the level of the medial malleolus at an anterior site, sensation may also spread to the foot. The sensation may be experienced as a warmth, tingling, a fluctuating pressure, and diverse types of electrotactile sensations.

In an additional embodiment, the third band 60*a*' can operate in conjunction with the second band alternate between providing three stimulation protocols including stimulation between a) a posterior medial electrode and anterior medial electrode, b) a posterior medial electrode and an anterior medial electrode on the second band 60*b*, and c) an anterior medial electrode and the medial electrode on the second band 60*b*. Further the three stimulation montages can each utilize its own stimulation protocol parameter values (e.g. amplitude). In this manner the stimulation may be provided to both the PTN and the SAFN nerve using different stimulation paths. A design which uses either only the third band 60*a*, or the third band 60*a*' and the second band 60*b* may not provide as much therapy benefit as using the first 60*a* and second 60*b* bands because less of the SAFN fibers may be activated by TENS of the bounded region 63.

Alternatively, in an embodiment a circumferential band 60*a* may be designed with a horizontal electrode gap of approximately 1 to 2 inches to stimulate both anterior and posterior to the medial malleolus, to provide both anterior saphenous and PTN stimulation treatment.

In an alternative embodiment, band 60*b* and conduit 62 are configured to enable the band 60*b* to reside at a lower leg portion 63 of the patient's leg. This may include provision of a longer conduit of at least 4 inches, and smaller band length to accommodate the smaller circumference of the ankle region. The lower band 60*b* has at least one electrode positioned posteriorly so that the PTN may be stimulated (or anteriorly so that the anterior SAFN nerve branch may be stimulated). The two different nerve targets are stimulated by the same stimulation waveform. For example, a first electrode pad can be provided on the top band, and a second electrode pad can be provided on the lower band, and the stimulation waveform can travel therebetween. Alternatively, the first and second bands may each have an electrode array of at least 2 electrodes and a first waveform can stimulate the PTN. The electrode arrays of either the first, or second band, or both may be oriented horizontally, in order to be applied in a circumferential manner or may be vertically offset so that one is more proximal and one is more distal along the leg. Using a vertical offset may allow for a larger distance (and thus larger fields) to be realized between electrodes.

When both the PTN and the SAFN are stimulated, the calibration, setup, and therapy stimulation for each may be done at separate times so that stimulation can be independently assessed and adjusted for the 2 targets. It may be difficult for a patient to assess the stimulation of the SAFN which may be experienced as a sensation that radiates from the top band located below the knee down the leg towards, and even to, the level of the medial malleolus. This difficulty is increased when stimulation is concurrently being provided by 1 or more electrodes of the lower band adjacent to the region of the PTN. Accordingly, after the stimulation protocol has been established for the SAFN, that stimulation can be halted while the stimulation of the PTN is established. Establishing a successful protocol for the SAFN will may typically involve confirming nerve recruitment by way of a sensory response along the SAFN fiber network, while PTN stimulation is confirmed using a motor response in the foot. Stimulation systems for the PTN that do not evoke motor responses are not anticipated to provide clinical benefit. After stimulation of both targets has been validated, treatment can be provided at both targets using a therapy protocol and associated waveforms.

The bands 60*a*, 60*b* can be made of comfortable materials such as cotton and stretch fabrics (e.g. fibres using neoprene or 'elastomerics') such as spandex or elastane (i.e. 'Lycra'). Various mechanical based fastening solutions such as "Velcro®" as well as rubber, plastic, and/or silicone-based endo-/exo-skeleton features that permit the support structure to be easily secured to a variety of different calf shapes and sizes and adapted/positioned according to individual preferences. A fastener such as a side- or center-release buckle, side squeeze clip, snap, or other type of securing means can secure the band once the circumference has been adjusted. In embodiments, bands use conductive fabric or dry electrodes to provide stimulation.

FIG. 3B shows an alternative embodiment where the system is configured with an extension component 66, which allows the stimulation waveform to be transmitted to a site which is below the band 60*a*. In an embodiment the electrode array used with the device 64*b* is contoured with a first portion that remains within the band 60*a* and a second portion that is shaped to provide an electrical stimulation at an electrode below the level of the band in the extension component 66. Additionally, in an embodiment, a second flexible band 60*c* may be provided to keep the extension component 66 in place and reinforce the electrical skin contact of the array. The extension component can be attached to the band 60*a* so that it remains biased against the patient's skin. For example, a biasing mechanism (e.g., 97 shown in FIG. 5) such as rotatable hinge having a spring can be deployed between the band and the extension 66 to bias the extension 66 against the leg. The band 66 is shown with a vibrator 39 that is powered by the device 64*b*. The device 64*b* may also reside within/upon the extension component 66.

FIG. 3C shows an alternative embodiment where the width of the band 60*d* along the leg is increased relative to that shown in FIG. 3B. For example, instead of the width of the band being 2-3.5 inches, the width of the band may be increased to 5-6 inches in order to provide greater vertical displacement between electrodes, or to use electrodes that are displaced circumferentially but have a greater distribution along the vertically oriented y-plane. The width of the electrode array may be increased from about 2 inches to 4 inches (y-axis). This may also allow for the spacing of the electrode array along the y-axis to be increased in order to provide stimulation to electrodes that are separated vertically (e.g. by 1-3 inches) as well as, or in alternative to, circumferentially (i.e. along the x-axis). Further a first conduit 68*a* is provided to communicate electrical signals to and/or from a first accessory 70a. This may be realized as a conventional TENS electrode that can be positioned distal to the band. A second conduit 68b electrically connects a second accessory 70b which may also be a conventional TENS electrode positioned proximal to the band. Instead of a first conventional TENS electrode, the accessory 70a can contain a vibrator stimulator 39 used to assess successful recruitment of nerve by electrical stimulation. For example, positing the vibrator 39 below the band 60d can allow an individual to determine if electrical stimulation provided at the level of the band 60d provides sensory masking of the vibrational sensory stimulation. The accessory 70b can also be realized as a heat or cold source that is frozen or heated before being applied to a user. Alternatively, Peltier or other means of electrically modulating temperature may be used.

For some embodiments the rotational arrangement of an electrode array within the band 60d is important. Visual indicators 71 (shown as letter markings) allow the electrode array and band to be worn with the correct angle of rotation so that the intended target area is stimulated.

The band 60d can be positioned to stimulate in the upper calf region 61 by positioning the array on the skin and then tightening band to bias the array against the skin of the patient and assist the adhesive on the electrode to maintain good electrode-skin contact during use. In an embodiment, the electrode array should be sized and configured so that it will apply intended electrical stimulation to the appropriate anatomy of the patient when the rotational position of TENS apparatus on the patient's calf is appropriate and markings on the array, the band, or otherwise should be provided to ensure correct alignment.

Figure 6A:
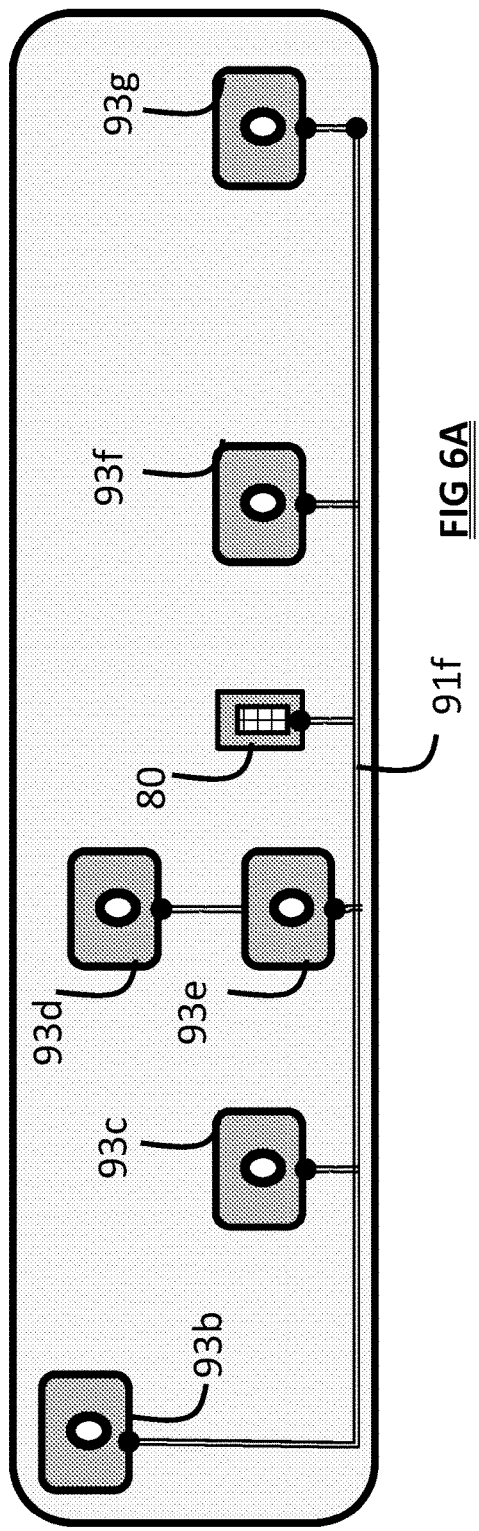
FIG. 6A is a schematic view of the front side of an example electrode array used with the TENS apparatus of FIG. 1A.
Figure 6B:
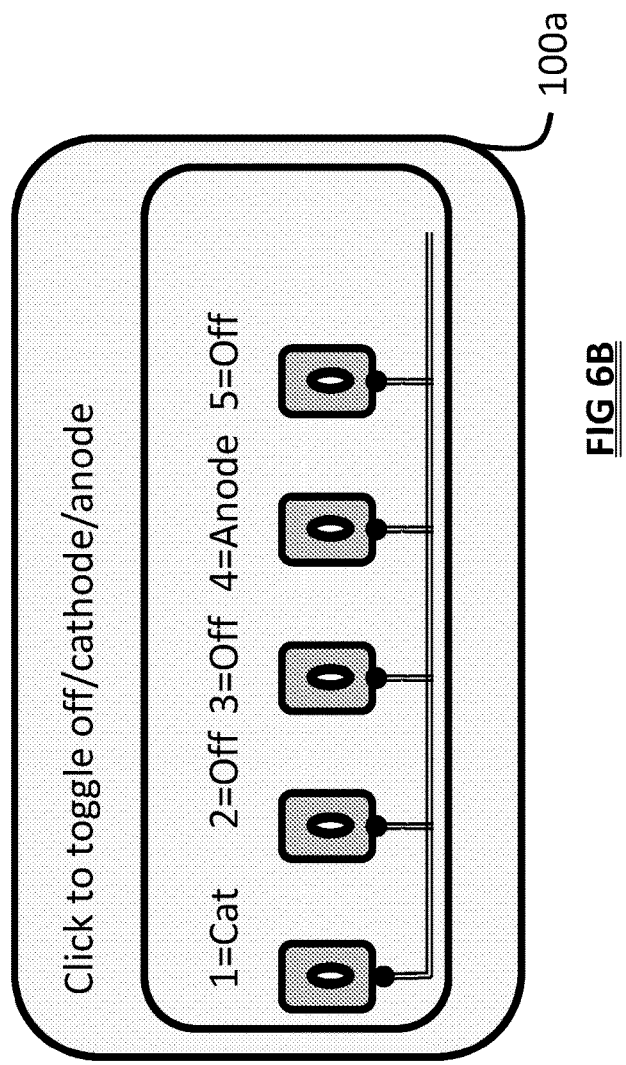
FIG. 6B is a schematic view of a programming screen which allows for display and/or user adjustment of stimulation settings for an example electrode array used with the TENS apparatus of FIG. 1A.

In an embodiment, the provision of software and/or hardware allows a user to dynamically toggle what electrodes are used for stimulation (see FIG. 6B). In one embodiment, the band may be configured with orientation markers 71 (see FIG. 3C), such as colored LEDS or simply numerical markings. When LEDs are used, a user may operate software to cause the LEDs, which are at locations of the electrode pads, to light up in order to indicate which electrode sites of an array are active and what their rotational locations are. The band, electrodes, or electrode array may also have numeric markers which correspond to each electrode site so that the user can see what electrodes are placed over the intended areas to be stimulated and can differentially activate the individual sites. FIG. 6B shows a graphical user interface 100a that allows users to define which electrodes are active and also assign cathode/anode that provides increased patient comfort.

Figure 3F:
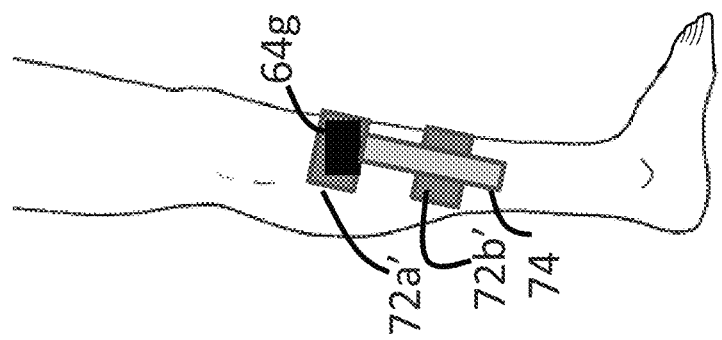
FIGS. 3D-3F are schematic views showing additional embodiments of TENS systems mounted to a lower leg of a patient.
Figure 3E:
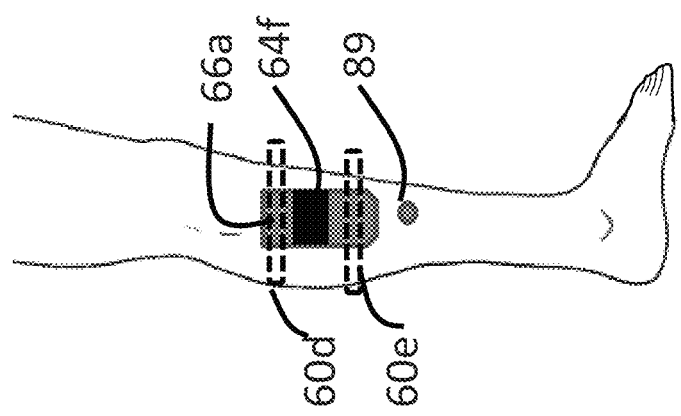
Figure 3D:
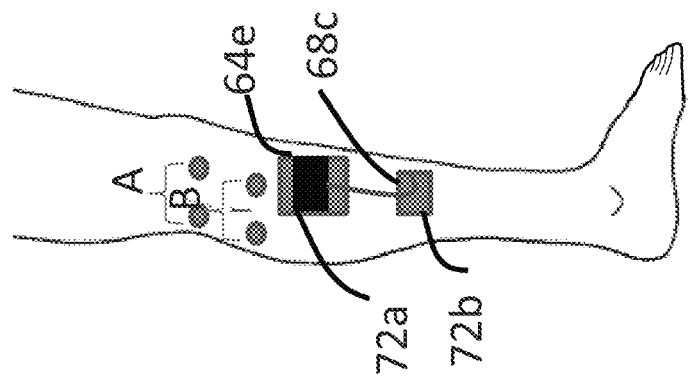

FIG. 3D shows an alternative embodiment where the TENS stimulator 64e is mounted on a first TENS electrode pad 72a having an electrical contact which snaps to the bottom of the stimulator device 64e to provide an electrical path from the stimulator to the patient's skin. A second TENS electrode pad 72b, having at least one electrode contact, is connected by a conduit 68c to a connector port provided either on the TENS stimulator 64e or on the first TENS electrode pad 72a. While the wire-free TENS device shown in FIG. 3B does not have any free-standing wires, the diversity of human leg length and shape may have sufficient variance that it is not desirable to have "one size fits all" device. The system shown in FIG. 3D may accommodate a larger range of human leg shapes and sizes and has only one conduit which is less than a conventional TENS system.

In an embodiment, two electrodes are realized on the first electrode pad 72a. The electrode pad may be realized using a limited number of sizes such as "small", "medium", and "large", corresponding to for example, approximately 3-5, 5-7, and 7-9 inch gaps between the electrode pairs. The spacing can be arranged to accommodate variance in the length of the human leg. The number of sizes and electrode pair spacing or "gaps" for each size can be determined using anthropometric modelling of human population data on leg size and geometry and/or anthropometric database (e.g. CEASER).

In pilot experiments done by the inventors, using 1.25" Round Tan Cloth Electrodes (TYCO Gel) TENS electrodes, most subjects did not experience electrotactile sensation which extended distal from a pair of electrodes placed horizontally on the medial aspect of the knee at locations approximately shown in FIG. 3D (labeled as "A" and "B"). Although the SAFN may be modulated by such an electrode arrangement, the failure to subjectively feel the stimulation may indicate less of the nerve is recruited. A vertically oriented electrode array may produce stronger therapeutic benefit.

FIG. 3E shows an alternative embodiment where the TENS stimulator device 64f is mounted on a first TENS electrode pad 66a (a vertically oriented electrode array of at least 2 electrode contacts) which snaps to the bottom of the stimulator 64f. The pad is held in place by an adhesive electro-conductive gel and by at least a first band 60d, although a second band 60e may also be used. In addition to, or rather than, using electrodes the wearable stimulator 64f can be configured with a stimulation module 48 that contains coils or other transmitter that controls operation of an implanted device 89. When both external and internal stimulation are supplied, these can complement each other. In an embodiment, the pad and device can be realized as a disposable TENS.

FIG. 3F shows an alternative embodiment of a system that allows for a fixed, but adjustable, distance between electrodes to be obtained during each use. The TENS stimulator 64g is mounted on a first TENS electrode pad 72a' having an electrical connector on its top side which snaps to the bottom of the stimulator 64g. The electrode pad 72a' provides a first electrode contact on the bottom of the pad to stimulate a user's skin. There is also provided a second pad 72b' that provides a second electrode contact on the bottom of the pad. The first and second pads 72a', 72b' are separated from each other in an adjustable manner by having a user slide the second pad along a flexible or rigid track 74. Electrical connection is maintained between the first and second electrode pad 72a', 72b' either using a free-standing conduit that connects the two pads, or by a conduit (not shown) routed along, or attached to, the track. The adjustable track can have markings permitting a user to slide the second pad 72b' along the track to a predetermined length suitable for that user. After therapy a user can slide the second pad towards the first in order obtained a "closed" position and compact shape. In an embodiment, the distance between the first and second pad is either sensed automatically or input by the user into the device 64g. The inter-electrode information is used algorithmically or by a look-up table of reference values stored in the control module 40 to determine adjustments to protocols related to providing, adjusting, or assessing stimulation, or measuring impedance.

Treatment Programs

Although devices are typically disclosed using single-leg examples, a patient may use the system 8 on one or both legs depending on symptom type and severity. In the case of two TENS devices 12, these may have wireless communication protocols in the communication module 52 that coordinate their operation. Cooperative operation may comprise stimulating at the same time, in an alternating manner or otherwise. The stimulation parameters may be set differently for the two legs.

Stimulation signal strength can vary in relation to how long the stimulation is provided. When stimulation is provided daily, and for more than 30 minutes, it may be that stimulation for either PTN or the SAFN can be reduced to a level which is slightly above nerve recruitment level while still providing sufficient therapy to the patient. It may also be that some patients can receive therapy benefit even if the stimulation is provided below a level where they feel the stimulation.

The TENS stimulator controller 40 operates according to a microprocessor-control circuit that can control the other components of the device such as a digital-to-analog (D/A) waveform generator or an analog stimulation waveform generator. When sensing is used an analog-to-digital (A/D) converter may also be provided. The waveform generator can generate various waveforms such as a monophasic pulse train or a biphasic, symmetrical, rectangular pulse train with regulated current. The stimulation pulse waveform is preferably charge-balanced to deter charge build-up under the electrode array and associated skin irritation. Either constant current or constant voltage pulse stimulation paradigms may be used.

In order to sufficiently address impedance/resistance variations caused by variations in skin types, skin thicknesses, hairs and oils on the skin of an individual, and variations in electrode conductivity (due to repeat use) the maximum output voltage typically provided in TENS units can be set as high as 100V and the maximum output current is 100 mA.

In the treatment of pain, a typical stimulation protocol can utilize a pulse pattern which comprises continuous stimulation or stimulation that varies below, or both below and above, 10% of the treatment value amplitude setting. The frequency of stimulation can be set between 60 and 100 Hz and may be constant or may randomly vary the inter-pulse intervals so that the instantaneous frequency of stimulation varies between 60 Hz and 100 Hz. In the treatment of overactive bladder, the frequency of stimulation can be set between 1 and 50 Hz, preferably between 5 and 20 Hz, or 10 and 20 Hz, or may simply be set to be constant at 5, 10 or 20 Hz.

When the stimulation varies, it may be implemented in random fashion, with a uniform or other manner across a selected frequency range, but may also be set to repeatedly rove upwards and/or downwards, in a smooth and continuous fashion if this is found to be more comfortable or efficacious to the patient. Smooth transitions may be preferred when treatment is provided while sleeping. This protocol may be indicated by a user selecting a sleep-protocol, or due to time of a real time clock in the control module 40 indicating the time is between 10 p.m. and 7 a.m.

An advantage of frequency variation of stimulation in OAB treatment is that while many patients show benefit at 20 Hz, some may show greater benefit at 5 or 10 Hz. Accordingly, the chance that the stimulation is provided at a frequency that provides symptom relief may be increased. In an embodiment, there may be 3 protocols provided, one at 20 Hz, a second at 5 Hz and another at 10 Hz. The patient may select a different protocol if therapy benefit is not obtained after an induction/assessment period which may be set, for example, as 1, 2 or 4 weeks.

In embodiments, the stimulation attributes used to generate the stimulation waveform are programmable. Programmability can be achieved with the stimulator connected in a wired or wireless manner to the user's device 32 such as a smart phone, smart watch, or computer that is running software which allows adjustment of the therapy program either before or during the provision of therapy. In the treatment of OAB the stimulation frequencies should be limited to between 2 and 50 Hz, or 1 and 20 Hz, or 5 and 20 Hz. Modulating a fast carrier signal (e.g. 50 kHz) by a slower rate (20 Hz) or using interferential stimulation strategies with two or more pairs of electrodes may be used to provide advantages with respect to transmission of the signal through tissue.

In an embodiment, the stimulation can be used to increase the probability of urination by the user setting the stimulation frequency in the 50 Hz range, or a range between 40 and 60 Hz, to increase bladder activity (e.g. to treat urinary retention). Additionally, at least in some users, it is possible that 50 Hz activity may be used in some patients to decrease incontinence because stimulation in that range acts to cause constriction of the urinary sphincter or modulate the bladder neck in such a manner as to limit flow of urine out of the bladder and prevent leaks.

In an embodiment, the band is used to house the electrode array and does not include the stimulator 12. The system band, device, or electrode array components may each include electronic circuitry, that can assess and/or measure properties such as distance between electrodes, calf circumference, skin temperature (by providing a thermometer or heat sensor on the device or array, with associated circuitry in the 50 sensing module), movement or posture (e.g. lying down or walking) and/or other types of user data (e.g., bloodflow, impedance etc) which can be used to adjust stimulation protocols and parameter values.

Electrode and Electrode Array Designs

FIG. 4a shows the first (back) side of an embodiment of an electrode array 18 in which electrodes 90a, 90b, 90c, 90d are connected by conductive traces 91a, 91b, 91c, 91d to connection port 80 (shown as port 24a in FIG. 1A) having contacts 82. The traces are realized as printed conductive traces (e.g. silver), which are covered with an insulating material, or are formed as electrical routing using a comparable solution, as is well known. The traces can be substituted by insulated wires. In an embodiment, the conductive traces 91, and contacts 82, are configured so that electrodes 90 serve to form sets of two or more electrodes. Each electrode serves as anode or cathode to complete an electrical circuit. For example, 90a can be an anode and 90b can be a cathode, or vice versa. When two electrodes both serve as anode (or cathode) these may be electrically connected to the same conductive trace (or to each other) to receive the same waveform. For example, 90a and 90c may receive the same waveform carried along tracings 91a and 91c. In this case tracing 91c may be electrically connected to tracing 91a rather than being connected directly to a common contact 82 of port 80. The stimulus generator is configured to deliver distinct waveforms to the different electrodes 90a-90d using fixed circuitry and where conductive traces 91 are connected to specific contacts of the port 80. Alternatively, the stimulation module 48 may include dynamic routing circuitry of the device 12 to route signals to electrodes in a selectable, programmable manner. When the polarity of an electrical pulse of the stimulus waveform is reversed, then the roles of the cathode and anode electrodes are also reversed. The assignment of anode and cathode can be dynamic and instantaneous. Generally, it is understood that the array arranges electrodes with a horizontal orientation when residing in a band and these are positioned circumferentially during use. Although there is some vertical offset, they are not considered as vertically offset since this would typically indicate very little overlap, and preferably a gap, between the top and bottom edges of adjacent electrodes The minimum distances between electrodes may depend upon the application. A preferred embodiment minimum distance is about 1 inch, but this can also be modified depending upon the size of the electrodes. If the cathode and the anode are too close the stimulation current may not travel deeply enough to modulate the target nerve tissue. Making the electrodes smaller can serve to increase the charge density especially near the electrodes, making the maximum intensity which a subject may tolerate to be lower than that which would be output by the device if a larger electrode was used.

FIG. 4B shows the second (front) side of an embodiment of the electrode array. The electrode pads 92a, 92b, 92c, 92d are comprised of a conductive adhesive gel that is affixed to the electrode backings 90a,b,c,d each of which have a conductive element attached to the conductive traces 91. Although the routing traces and pads are shown residing on the back and front sides of an electrode array, all components can reside on the front surface of the electrode array substrate material. The array is designed to allow physical and electrical connection between components on the back and front sides, as is well practiced. The connection port 80 is typically located on the back side of the array to allow mechanical and electrical connection to its corresponding connection 24b on the device 12. The electrode pads 92a-d have a selected size, shape, and separation to provide stimulation of a target nerve related to treatment of a disorder.

In an embodiment, electrodes are positioned on an array designed to treat pain, regardless of the rotational position of electrode array 18 relative a patient's leg. When providing stimulation circumferentially using electrodes 90a,90b,90c and 90d, or otherwise, stimulation of a non-target area may cause side-effects such as muscle stimulation or discomfort. Stimulation of non-target areas may also decrease the maximum tolerated stimulation signal since a non-target area may be more sensitive to stimulation. Accordingly, in an alternative embodiment, stimulation can be directed towards a specific nerve target or target skin area with electrodes that are shaped and positioned at specific locations (e.g. using only 90b and 90c to target the SAFN on the medial aspect of the leg). Although the electrodes may be connected in an interleaved manner (i.e. pos, neg, pos, neg) they may also be connected so that the two adjacent electrodes are electrically connected and/or otherwise operated as anode or cathode. Pairs of electrodes such as 90b/90c and 90a,90d can be powered by the same conductive tracing circuit (i.e. tracing circuits 91b and 91c can be powered from the same contact 82 on port 80).

FIG. 4B shows two alternative embodiments for the electrode array. Instead of electrode pads 92 each existing as electro-conductive gel pads, each pad is designed with an electrical snap 93a configured to allow connection to a disposable pad 95 having a complementary electrical connector snap 94a on its back side 95a that connects to a conductive material which interfaces with an electro-conductive adhesive gel on its front side 95b for connection to the patient (see FIG. 4C which illustrates the front and back sides of the disposable pads 95, respectively). In an embodiment, the disposable pad also has a pull-tab 96 to allow a user to pull the pad while detaching it from the array 18 during replacement. A backing or "carrier" as well as a primer can be used as part of the design as is well known in the field of adhesion/bonding sciences and a chloride based solid gel can relay the signal to a silver, silver chloride (Ag/AgCl) backing which transmits the signal to the conductive connector 94a.

In another embodiment, a disposable pad 95' is configured to adhere to an electro-conductive gel pad 92d, and includes an electrical gel pad (e.g. a latex free solid gel) on both its back-side 95c, and its front side 95d, with electrical connection therebetween. The adhesiveness of the gel pad on the back side which connects to the gel-pad 92d is configured to have a greater adhesiveness than the surface that is attached to the patient's skin. Because the adhesive strength is greater on the back of the gel pad 95', the gel-pad should typically disconnect from the user's skin rather than from the gel-pad of the electrode array 18. The gel pad 95' may also be realized as a "blocking pad" having an adhesive on its back side 95c and simply a non-conductive surface on its front side 95d. The front side can be sticky or can be connected to, for example, gel pad 92c, or any other gel pad. Blocking pads are used when stimulation is not wanted. This allows for customization of the electrode array in terms of which gel-pads provide stimulation to a user.

The provision of disposable gel-pads 95, 95' allows for cost savings since replacement of an entire electrode array is not required. Use of disposable gel-pads offers advantage for a user with more leg hair, oil, or other impurity (especially if localized to a region stimulated by a single gel pad) since it allows for the replacement of a single pad rather than wasteful replacement of the entire electrode array. Further, providing disposable gel-pad with different adhesiveness will suit some users who benefit from gel pads that have increased adhesion strength. Gel-Pads classified with a "stickiness rating" of 1, 2, and 3 can be offered to users. Other users will seek less adhesion to avoid such issues as skin irritation. Gel-pad 95' may be realized with a variety of characteristics. Adhesive and conductive materials can be chosen that are well suited for a given individual. Due to skin type, activity level, or other factor, a stronger adhesive may be warranted for some individuals and electrode pad gel designs may be oriented towards "high tack" (immediate adhesion) or for "high adhesive" (long term adhesion) and may be designed to allow the skin to breathe. A patient who will use the stimulation while sleeping may benefit from a different gel-pad property than one who uses the stimulator while being active and/or sweating, which may require a highly conductive solid gel with strong adhesion and high vapor transmission rate. Materials and TENS electrode designs that may be used to realize the electrode pad designs are disclosed in: U.S. Pat. No. 4,736,752, entitled Transcutaneous medical electrode; U.S. Pat. No. 8,634,895, entitled Biomedical surface electrode; U.S. Pat. No. 8,320,988, entitled Multi-electrode strung on a common connector; and, U.S. Pat. No. 8,825,128, entitled Sensor for measuring biosignals, all incorporated by reference herein.

As is well known, the backings of the electrodes 90a-d may contain a conductive silver pattern overlaid with a thin conductive layer of hydrogel (e.g. 92b). The backing for electrodes of the electrode array 18 can be selected to be Mylar on which the conductive pattern (e.g. mesh) is printed. Electrical routing between the electrodes 90a-d and the connectors 80 of the port 82 are realized by printed conductive traces which are covered with an insulating material. Further embodiments of electrode array 18 are contemplated including variations in the number, sizes and inter-electrode spacing. Alternative electrode conductive patterns such as a mesh, solid, spiral are within the scope of the present invention.

Figure 5:
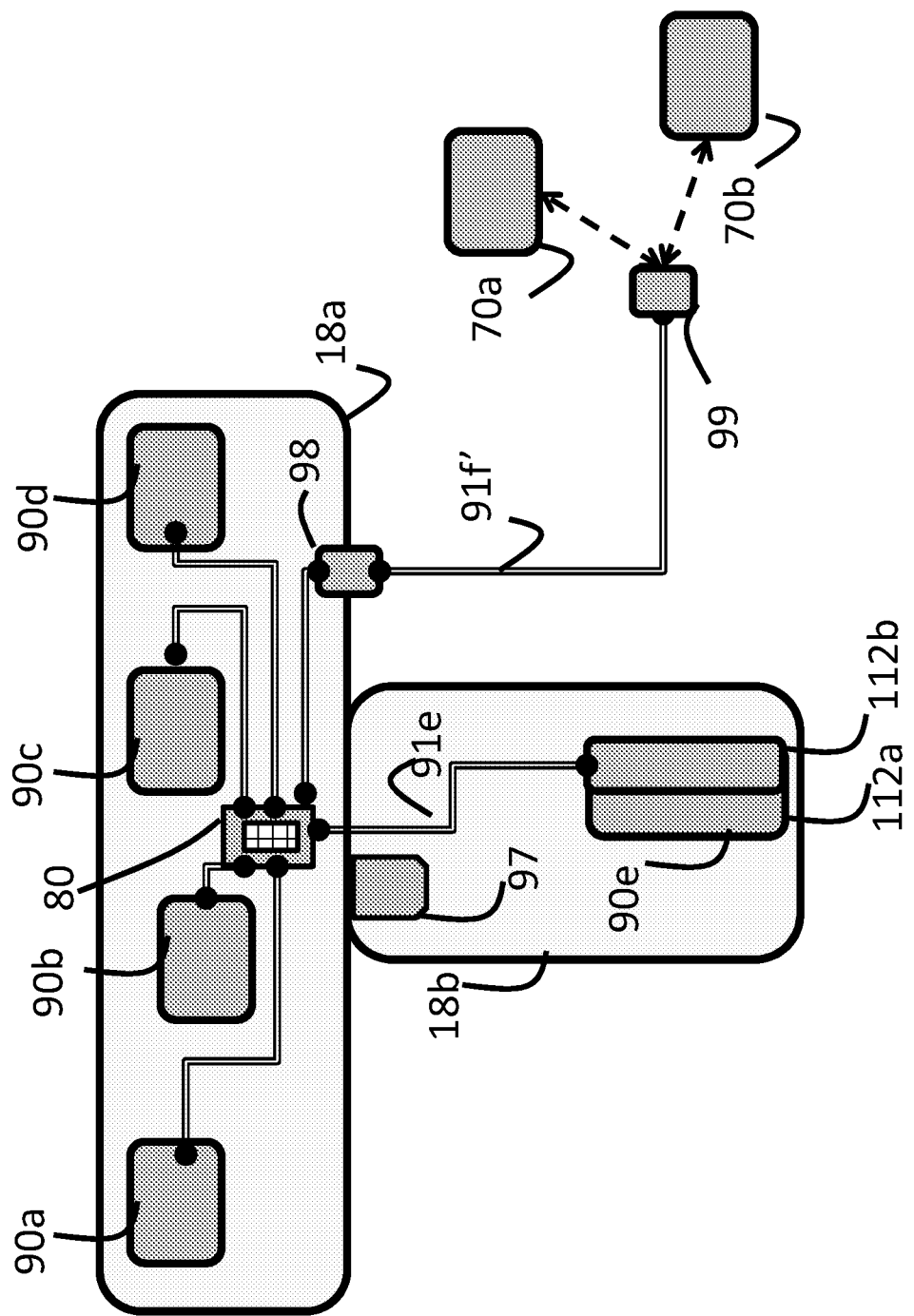
FIG. 5 is a schematic view of the back side of an example electrode array used with the TENS apparatus of FIG. 1A, and also includes an accessory port.

FIG. 5, shows a horizontally oriented electrode array 18a which is perpendicular to a vertical electrode array portion 18b that provides an electrode 90e which is vertically offset from the 1 or more electrodes 90a-d of the array. Electrodes 90a-d are horizontally distributed and typically disposed within the band 16. It is shown in its deployed embodiment in FIG. 3B. At least one electrical conduit 91e communicates electrical stimulation signals from one of the contacts 82 (shown in FIG. 4A) on the connector port 80 to each electrode. A biasing mechanism 97 can be used to bias contact 90e against the user's skin. In addition to, or as an alternative to, the vertical extension provided by array 18b, an accessory port 98 provided on the array 18a allows connection of a multi-stranded wire 91f that terminates using one or more accessory connectors 99. The connectors 99 allow attachment to at least one plug of one or more standard TENS electrodes. The figure shows the back-sides of the arrays that typically faces away from the patient's skin. This embodiment is for illustration purposes, and the tracings (e.g. 91e) and various components of the array could be disposed on either the back or front side of the array.

Alternatively, the accessory port 98 is configured with multiple contacts and can communicate electrical signals between the accessory port 98 and an accessory connector 99, which allows for connection to at least one accessory 70a, 70b. The accessory can simply be a TENS electrode which allows for provision of stimulation or sensing, or can be a vibrating stimulator which allows for masking of the sensations associated with electrical stimulation signals or allows a patient to assess a change in sensation that may occur when electrical stimulation is provided to any subset of the electrodes of the array 90a-d.

Electrode arrays having components that are adjustable, selectable, and customizable can provide advantages of increased recruitment, selective nerve recruitment, decreased electrical activation of adjacent nerves or muscle, and increases in goodness-of-fit with human legs or body parts that can be in the form of many different shapes and sizes. Embodiments which allow the electrodes to be selected so that signals can be programmatically or at least dynamically provided allow for customization of the stimulation field provided during treatment.

FIG. 6A shows an electrode array having electrode pads 93b-93g configured for use with disposable electrode pads 95. The orientations, inter-electrode pad distances, shapes, and sizes shown here are for illustration purposes. The number of electrode pads may also vary. The electrode array can attach to the device in more than one relative orientation. The electrode array is shown in a horizontal orientation. It may be configured to be rotated 90 degrees and attach to the device 12 in a vertically oriented position. A second port 80 may be provided to enable connection in the vertical orientation. In the illustrated embodiment, the leftmost pad 93b is configured at a position that is both vertically and horizontally offset from pad 93c. When stimulating the SAFN, a first electrode pad may be positioned medially just below the patella while a second electrode pad is used about 5 inches lower and closer to the palpable ridge between the tibia and the (medial) calf muscle. Accordingly, using two electrodes in the array that are both vertical and horizontal offset (i.e., diagonally displaced) may provide improved stimulation of the SAFN. If any of the electrode pads 93b-g are not used during therapy, they may have a non-conductive electrode-like disposable pads snapped into place during treatment to deter dirt or gel from adhering to the pad 93. Electrode pads 93d and 93e have a vertical offset and may be useful for stimulation therapies where at least two electrodes are placed on the leg so that one is more proximal and one is more distal, without additional benefit being derived by a diagonal distribution. Pads 93f and 93g are two pads which for horizontal offset when the pair is used to provide stimulation.

FIG. 6B shows a graphical user interface screen 100a as may be presented on software of a user controller device 32. The display can present a graphical distribution or depiction of electrode pads which may be programmably assigned values such as "on", "off", "anode", or cathode ("Cat"). A user may click on a picture of the electrode to change its state. Additionally, 2 electrodes may be designated as active (or anode) while a third serves to complete the electrical circuit (cathode). The software serves as part of the routing module 54 and collaborates with the circuitry and routines of that module to cause the stimulation signals to be routed and toggled appropriately. The provision of selectable or adjustable electrode arrays addresses several problems. For example, in the case where a patient has a small circumference calf, or if a child rather than an adult is the intended user then electrode pairs can be chosen so that the electrode spacing can be made shorter. Several types of problems, such as the electrode array being shorted, may be avoided using a selectable electrode array. Further, electrode combinations can be selected until desired nerve recruitment is successful or until side effects such as muscle stimulation are avoided.

In an embodiment, the electrode array shown in FIG. 6A can be realized as a grid (e.g. a 5×5 grid) with rows and columns of electrode pads. Each pad may be an electrode or may have "snaps" and upon which disposable electrode pads can be snapped. The conduits that conduct the electrical signals to the pads, can be realized as conductive traces or can be wires that are attached to the array and routed along a non-conductive set of pathways. When a grid is used, an interface can be provided that allows the user to shape or locate the electrical stimulation in customizable and intuitive manners. For example, the user may cause the stimulation field to become spatially biased either medially, laterally, proximally or distally along the leg using a touch sensitive grid displayed on the user device 32. The system 8 is programmed to use the input to adjust the pattern on the grid in a comparable manner. The user can also adjust the field to be deeper or shallower with respect to the skin surface, and this can be realized by causing the distance between an anode and cathode to be increased or decreased by turning pixels of the grid on and off. For example, if in a 10×10 grid, making the top 3 pixels anode, the middle 4 pixels neutral, and the bottom 3 pixels cathode will create a shallower stimulation path than if the anode and cathode only contained 2 pixels and there were 6 pixels between them. Using an interface that allows a user to customize the field may allow for improved recruitment of a target nerve. This feature can be accomplished using algorithms provided within the routing module 54. This interface can also be used to adjust the region of overlap created by interferential stimulation waveforms.

In an alternative embodiment the back sides of the TENS electrodes can be provided with a material such as Velcro® (or adhesive). After the TENS electrodes are situated correctly on a user's leg (e.g., evidenced by an electro-tactile tingling that radiates down the leg). The user may then wrap a band 16 around their leg. This will cause the back of the electrodes to adhere to the band which also has a Velcro® surface. Alternatively, an array substrate material includes a foam core and has Velcro® material on its surface. The electrodes are secured to the array's surface at customized positions.

FIG. 6C shows an embodiment of an electrode array having an adjustable track 102. A second array 18d having 1 or more electrodes is slid along the track 102 to produce the desired inter-electrode spacing with first array 18c. In the illustrated embodiment, track 102 has electrical contacts 104 that relay stimulation signals to electrical routing 91g. Electrical contacts 104 serve as electro-mechanical fasteners that can be secured to complementary fasteners 106 on the second array 18d. Additional fastener elements 103a,103b may further secure the second array 18d to the track. An electrode array comprising a first and second array and adjustable inter-array (and hence inter-electrode) distance may provide improved nerve recruitment for individual users.

Instead of adjustable electrode arrays, electrode arrays of assorted sizes may be used. In an embodiment, a user is instructed to measure the circumference of a portion of their leg. This measurement is used to determine array size and/or electrode spacing. For example, electrode arrays are labeled Model A, B, C, D and E. The models differ in a characteristic such as electrode geometry, width, length, and/or inter-electrode spacing. The array models provide a good fit and address variation that exists across most (e.g. 95%) of the population. After accounting for differences in body size, determining successful locations for SAFN stimulation may be reasonably simple. A recent study has found that the SAFN only had 2 to 3 basic variations with respect to where the main fibers can be found between the knee and ankle in the human leg (Wilmot and Evans, *Categorizing the distribution of the saphenous nerve in relation to the great saphenous vein*. Clinical Anatomy 2013; (v26), 531-536).

In an embodiment, a system for providing transcutaneous stimulation to a patient comprises an electrical generator of a stimulation module 48 for providing a predetermined electrical stimulation signal, a signal router electrically coupled to said electrical generator for routing the electrical signals (e.g., such as to contacts of a port 24b), at least two electrode array members 18c 18d, each of said electrode array members having at least one stimulating electrode pad 90a for receiving at least one electrical signal from a signal router (e.g., via a port 80 and electrical routing 91g), a substrate (e.g., a band 60a) contiguous to at least one of said electrode array members, each of said electrode array members being displaceable with respect to said substrate; and, an adjustment member connected to said at least two electrode array members for selectively adjusting a position between said at least two electrode array members 18c,18d.

In an embodiment, a system for providing transcutaneous stimulation to a patient, comprises an electrical generator of a stimulation module 48 for providing at least a first predetermined electrical stimulation signal, a signal router electrically coupled to said electrical generator for routing the at least first electrical signal to at least one electrical contact on the housing 14 of a neurostimulator device 12 (which may be realized within port 24b). The system also comprising at least a first electrode array member having at least a first stimulating electrode for receiving at least one electrical signal from said electrical contact, and a substrate (such as a band) contiguous to at the least electrode array member, adapted to be contiguous with the skin of a user 8. The system further comprising an adjustment member configured to selectively adjust at least one of the following: a) a position between an electrode on the electrode array and the substrate, b) a position between the first electrode and at least a second electrode; and c) a position between the first electrode array and a second electrode array. The adjustment member can be a physical, such as the track 102 along which an electrode array is positioned, or a series of electrode pads that are configured to receive electrodes via snap connectors, or can be electronically realized use a graphical user interface to position actively electrodes 100a.

FIG. 7A shows an embodiment of a band 16 which is configured for engaging with a horizontal electrode array 18 comprising first 28a and second 28b electrode pad, such that when the band 16 is deployed on user's leg, the electrodes are distributed circumferentially. The array connector port 24a on the electrode array 18 is configured with 2 metallic horizontally oriented snaps which connect to conductive tracings that route the stimulation signal to the electrode pads 28a, 28b.

FIG. 7B, shows an alternative embodiment, where the array connector port 24a on the electrode array is configured as 2 metallic horizontally oriented snaps which connect to conductive tracings that route the stimulation signal to the electrodes 28a,28b, which are positioned upon a vertically oriented electrode array. Using these two array designs a band 16 and device 12 can be used with either a horizontally or vertically oriented electrode array. Flexibility of array orientation allows the provision of multiple therapies to a user, without a user being required to obtain 2 different bands 16 or devices 12. In the first design, the electrodes are aligned with the axis defined by the two contacts of the electrode array, while in the latter the electrodes 28a,28b are perpendicular to this axis (and aligned with the axis of the limb).

Figure 8:
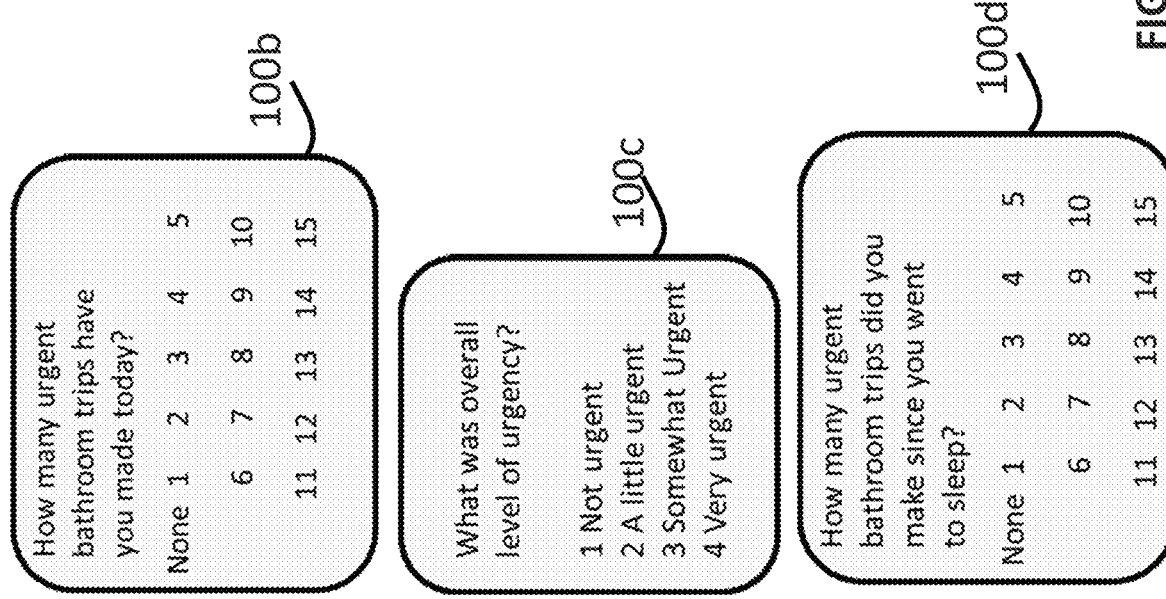
FIG. 8 shows 3 different screens which allow users to provide information related to symptoms.

FIG. 8 shows an embodiment of screens 100a, 100b, 100c that allow entry of data related to treatment of a disorder, such as OAB. The screens allow assessment of number of urgent voids experienced that day 100b, overall degree of urgency of bathroom trips 100c, and nighttime bathroom trips 100d. Additional screens enable survey of the patient on other aspects of the symptoms, quality of life, amount of urine voided, number or frequency of accidental leak. The screens are presented to the patient by the monitoring module 46 at specific times such as 10 p.m. and 8 a.m. or the patient may invoke the screens as desired. The screens are also configured to allow input of bladder diary data. These data can be organized by date and time. A digital version of the overactive bladder quality of life survey such as OAB-q may be used. Information is provided at times determined by the patient in response to prompts or reminders. For example, a smartphone application provides pop-up notifications or text message at scheduled times to cause the user to enter information about symptoms. The software application is also configured to provide prompts about behavior adjustment, such as prompting a user to visit the bathroom just prior to a time that has been defined as an event such as leaving for work or going to sleep.

Figure 9:
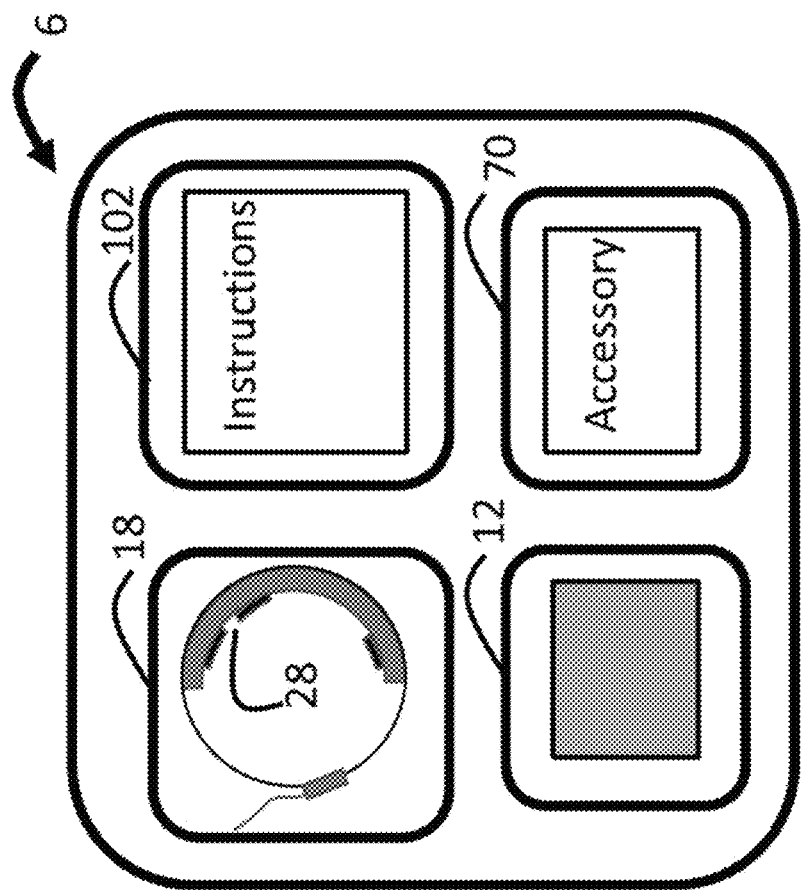
FIG. 9 is a schematic view of a TENS kit.

In an embodiment, shown in FIG. 9, the invention is realized as a kit 6 having at least one stimulator and two TENS electrodes 28 configured on an array 18 to receive a stimulation signal from a TENS neurostimulator 12. The stimulation signal can be provided according to a stimulation protocol that is defined for stimulation of the SAFN for the treatment of overactive bladder, for pain, or for a different disorder and the device 12 can allow a user to toggle between these treatment protocols. The kit also includes instructions 102 for using the neurostimulator 12 for the treatment of overactive bladder disorder which includes instructing a user to applying at least one of the 2 stimulators on the medial aspect of the leg at or below the knee for the stimulation of the SAFN. The instructions 102 may alternatively include instructions to place at least one of the two TENS electrodes on the inner side of the leg in the area near the upper calf and then provide a stimulation signal in order to determine if at least one of a tingling, vibrating, buzzing, pressure, tactile, warmth, or tickling sensation is experienced typically as radiating away from the location of at least one of the two electrodes. Further, the instructions direct a user in the case where the sensation is not experienced, and the application of the stimulation signal fails to produce a radiating sensation indicating that the saphenous nerve has been stimulated, to then perform the additional step of either increasing the stimulation intensity or re-adjusting the position of at least one of the two TENS electrodes. The kit also includes an accessory 70 such as a vibrator which can provide masking to decrease stimulation induced sensations that are not to the subjects liking, or to produce a sensory stimulus which will be masked when stimulation successfully causes nerve recruitment. In an alternative embodiment, the stimulation treatment of OAB, or other disorder, is provided using vibration to stimulate the nerve at a selected frequency. The kit may also include a user device 32 (such as a remote control, not shown), although the user will more typically install software on a smartphone.

FIG. 10 shows an embodiment of a system 200 for providing magnetic stimulation in the treatment of pelvic floor disorders. The system 200 has all the components of the device 12 shown in FIG. 2, as well as additional hardware that is needed to supply power to magnetic stimulators. The system contains one or more magnetic stimulators 202a, 202b, 202c. The stimulators 202a-202c are configured to reside on a support platform 204 which positions and supplies power to, and control of, at least one magnetic stimulator to stimulate at least one nerve target of a human leg. In the embodiment shown, the first stimulator 202a is configured to be positioned at or below the level of the knee to stimulate the SAFN at a first location. The second stimulator 202b is adjustably positioned approximately 3 to 8 inches below the first stimulator to provide stimulation to the SAFN at a second location. Alternatively, the magnetic stimulators can be positioned within a piece of furniture that can be used in a clinic or at home and can be positioned and oriented to stimulate a nerve of a user.

In an embodiment, third stimulator 202c is provided at a selected location and stimulation parameters to stimulate the PTN. The SAFN and PTN appear to provide at least partially independent modulation of bladder activity. Selectively stimulating the SAFN and the PTN may improve benefit compared to either alone. The stimulation signals can be pulse trains having frequencies of between approximately 5 and 50 Hz, and more preferably between 5 and 20 Hz when inhibition of bladder activity in the treatment of OAB is sought.

The PTN is deeper than the SAFN and requires a stronger field to achieve electrical activation. The waveforms of the first and second stimulators 202a and 202b can be different than that used at the third magnetic stimulator 202c. In an embodiment, stimulators 1 and 2 use coils and stimulation parameters to stimulate about 1 cm below the skin. Stimulator 3 is configured to provide penetration 2-3 cm below the skin.

The stimulators can be positioned to allow their fields to overlap at the tissue target. Using two stimulators may allow stimulation strength at either stimulator to be decreased compared to that necessary when using a single magnetic stimulator. A lower field strength requirement can permit less complex/expensive system design such as smaller coils and lower power criteria. This may also increase comfort compared to a larger stimulation signal provided at a single site. Multiple stimulators allow an increased stimulation field size for modulation of the SAFN network. Multiple-site stimulation may increase the number of modulated nerve fibers, or may more reliably recruit a particular set of nerve fibers. Using multiple stimulators may cause enhancement of a response along a subset of SAFN fiber tracts or may recruit multiple fiber tracts. Benefit may be derived by either a stronger, or greater number of, signals transmitted along the SAFN network towards pelvic and or central "circuits".

In an embodiment, the stimulation protocol at each stimulator is adjusted with appropriately—chosen stimulation parameters that will allow multi-source stimulation. For example, a stimulation parameter value (e.g., phase or delay of the stimulation signal) is adjusted at each stimulator so that the evoked neural response caused by a first stimulator (or stimulator pair) does not cancel-out, or interfere with, stimulation provided by the second stimulator. The adjustment of stimulation parameters is guided by a) population normative values b) recording the sensory nerve evoked potential at a more proximal location c) subjective sensations reported by the patient, d) nerve conduction velocity values that are measured for the patient or which have been derived from the population. For example, parameter values may be selected to cause a constructive summation of evoked neural activity, to produce a net desired frequency when integrating across stimulators, or otherwise.

When using two or more magnetic stimulators, the stimulation signals of a selected stimulator are adjusted while the remaining stimulators are paused to allow assessment of the stimulation by the patient or otherwise. The effect can be assessed (e.g., sensory or motor response such as fanning out of the toes in the case of PTN). When stimulators 1 and 2 are used to stimulate the SAFN, the protocols for stimulators 1 and 2 may be assessed independently, and may further be assessed together. During joint assessment, stimulation parameter values (e.g., the delay of the pulses for stimulator 2 relative to stimulator 1 may be adjusted by objective or subjective measures such as asking the individual to indicate what settings cause the largest sensory responses. A larger sensation can reflect greater SAFN recruitment. The above advantages and considerations of using multiple stimulation sites may extend to implantable or TENS based stimulation systems and methods.

In an embodiment, the system 200 may be configured with at least one magnetic stimulator 202a (or microwave or RF simulator) that is configured to power an implantable neurostimulator 206 that stimulates the SAFN. Neurostimulator 206 may only utilize electrodes provided on its housing. Alternatively, the neurostimulator 206 may use a conduit 207 that has electrodes that are positioned along its length to provide SAFN stimulation at multiple points along its length. The conduit 207 may extend down to the level of the medial malleolus in order to provide stimulation to the posterior or anterior SAFN and/or to a PTN target. Alternatively, two or more neurostimulators may provide stimulation to two or more targets in the leg.

In the case of SAFN stimulation, it is preferable to stimulate the SAFN while avoiding unintended electrical activation of other (adjacent) tissue such as calf muscle. In an embodiment, deterring stimulation of non-target tissue is accomplished by use of a shaped electrode. Rather than using a square electrode, a rectangular electrode may be preferable, with the length being at least 20% larger than its width, but length may also be 2× to 4× the width (e.g. 90e, of FIG. 5). The electrode length is the axis aligned with the length of the leg. FIG. 11a shows an electrode pad 110 oriented vertically which is longer than it is wide. The pad has a snap 94b for connecting directly (or by a conduit) to a TENS device. A strap 60c secures the pad to the patient although adhesive and electro-conductive gel may also be provided. Additionally, the edge positioned adjacent to the calf muscle is tapered to create a relatively weaker region of stimulation at the muscle compared to the relatively stronger field provided further away from the muscle and towards the tibia (field shaping). The pad may use a single electrode on its bottom surface and a return electrode may be attached elsewhere nearby using a port on the pad or the pad may include 2 electrodes that each conform to that shown in FIG. 11b. Electrodes with discrete edges may be preferred by some users who find that using such electrodes result in less muscle activation than when using a square or circular electrode.

As shown in FIG. 11b, a shaped electrode can also be realized as an electrode with a first portion of its bottom surface 112a comprised of non-conductive adhesive so that the electrode sticks to the user's skin across its entire bottom surface while it only stimulates from a second portion 112b of its bottom surface where the gel is conductive and in electrical contact with a conductive backing. Field shaping may be enhanced using two closely spaced electrodes.

Implantable Designs

Figure 12:
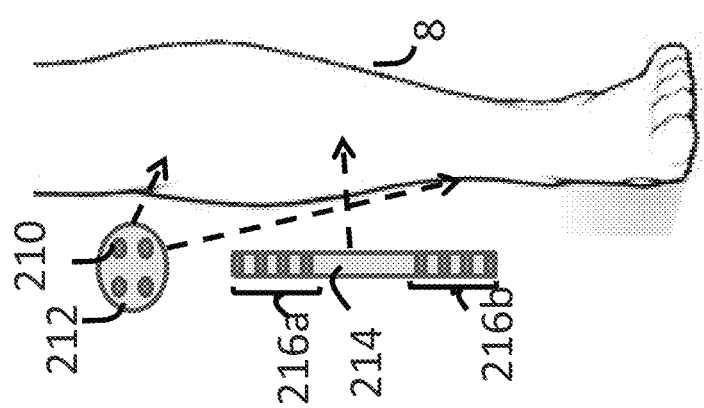
FIG. 12 shows implantable neurostimulator embodiments.

FIG. 12, shows two embodiments of implantable neurostimulators. In system embodiments having an implantable component, SAFN stimulation using an implantation site near the level of the knee may have advantages over stimulating the PTN near the medial malleolus such as: 1) evoking a sensory rather than sensory-motor response (i.e., extension of the foot or toes is absent or minimized) 2) providing a more appealing sensory experience as some users may find stimulation of the PTN less comfortable than SAFN 3) decreased risk of migration when compared to an implant placed near the ankle 4) decreased risk of breakage or damage due to a decrease in force, repeated movement and torque, and pressure relative to the ankle/foot region. While the implantable neurostimulator preferably has electrode contacts on its housing, its design may use conduits to route stimulation signals. The position of, and fixation strategy for, an implantable neurostimulator or its stimulators should decrease risk of migration. In an embodiment the neurostimulator housing is physically secured along the tibia or fibia in order to deter migration.

If a branch of the SAFN is located sufficiently near the implant location, then electrode contacts 210 on the housing of the neurostimulator 212 itself may be sufficient. Larger fields may be produced by neurostimulator designs that use conduits 214 with at least a first set of electrode contacts 216a or second set of electrode contacts 216b. The conduit can route the electrical stimulation signals to locations that are sufficiently close to SAFN and/or PTN targets so that they provide nerve stimulation. As the distance between the electrode contacts 216a is made larger the stimulation field may become more diffuse. In an embodiment, the electrode contacts may be spaced along a larger portion of the conduit to stimulate the SAFN at multiple locations.

In an embodiment, the neurostimulator 214 is realized as an elongated flexible conduit that is inserted with a trocar or introducer element just above the ankle and extends upward approximately 5 to 10 inches. A first set of electrodes 216a may be provided near the proximate tip to stimulate the SAFN. A second set of electrodes may be provided near the distal tip of the conduit 216b to stimulate the PTN. In a preferred embodiment, a pair of electrodes can be realized near both the distal and proximate tips to stimulate both the SAFN in the lower-calf region and at least the PTN at the region near the medial malleolus. Additional electrodes may be realized between the proximal and distal tips to provide additional stimulation sites along the SAFN network.

Dermatome Considerations

Figure 13:
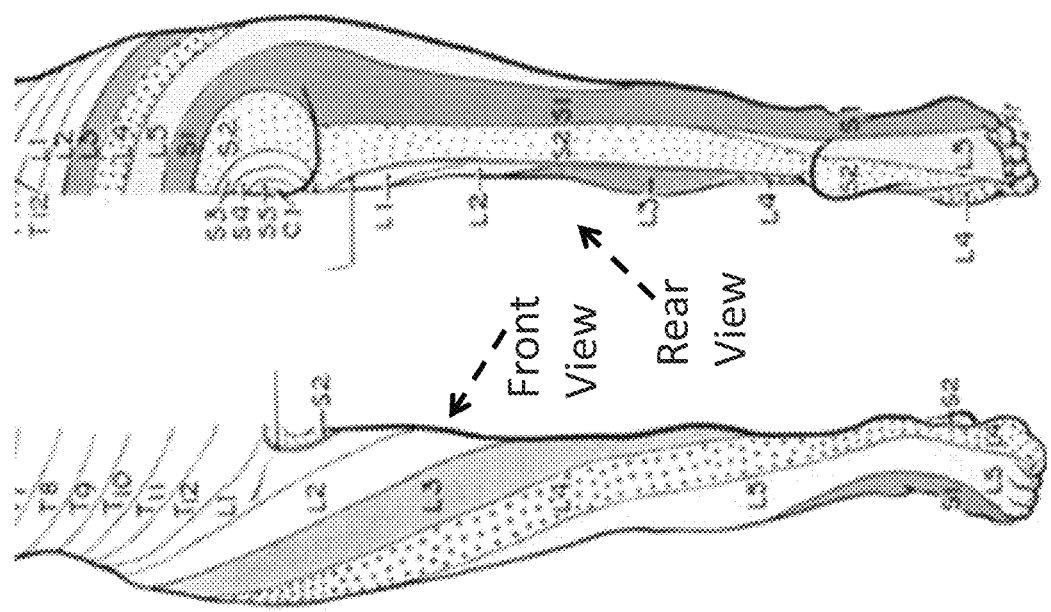
FIG. 13 shows dermatome maps relevant to selected stimulation sites and protocols.

Not to be limited by theory, since the SAFN sends signals to L3, L4, L5 spinal roots and has been shown to be useful in treatment of OAB, stimulation of the corresponding dermatomes may also provide therapy (See FIG. 13). The PTN sends signals to the S1, S2, S3 spinal roots. Accordingly, stimulation applied between approximately 1 and 50 Hz applied to the L2, L3, L4, S1, S2, S3 sensory dermatomes, with a preference for L3, L4 below the knee, may be successfully used to provide treatment for OAB. When stimulator 12 and electrode array 18 are connected together as shown in FIG. 2, and placed on the patient (using band 16) as shown in FIG. 1B, the individual electrodes 28a, 28b, 29 are positioned to deliver stimulation to the SAFN and/or L3, L4, between 1 and 50 Hz, and more specifically wherein 5 to 20 Hz, then this may provide treatment of OAB. Alternatively, individual electrodes (e.g., 28a, 28b, 29) can be positioned to deliver stimulation to the L3, L4, L5, S1 and S2 sensory dermatomes, and/or the sural nerve. Stimulation applied between approximately 60 and 100 Hz might successfully provide treatment for pain.

Using a full circumferential electrode, or incorrectly placed electrodes, may clearly stimulate dermatomes and/or underlying sensory nerves that are not relevant to the intended treatment. For example, in the treatment of pain, the patient may not require treatment of OAB symptoms, and vice versa. Further, in treatment of OAB if the lateral surface of the leg is more sensitive to stimulation than the medial surface of the leg then stimulation by an electrode positioned at the lateral area may limit the maximum stimulation level that might be achieved compared to the case where both electrodes are used to stimulate the medial area. It is preferable not to stimulate the calf muscle and accordingly, medial and slightly more anterior sites can be preferable to those near the muscle.

Additional Locations Useful in Treatment of Pelvic Floor Disorders and the SAFN

In an embodiment, a sensing electrode is used at a first site that is rostral to a second site of the leg at or below the level of the knee where stimulation is provided. The SAFN is a terminal sensory branch of the femoral nerve that innervates the medial surface of the leg relatively superficially at the level of the knee and down the leg. Above the knee, it passes within the subsartorial canal in the thigh and joins the femoral nerve trunk near the level of the inguinal ligament. Additionally, there are multiple locations (rostral to the knee) at which a percutaneous needle electrode can be used to record stimulation-evoked action potentials. Caudally, recordings of nerve activity may be also made near the ankle. At this higher level it is joined by other motor and sensory branches of the femoral nerve. In the canal and near the inguinal ligament, the SAFN lies close to the motor branches of the vastus medialis muscle. Just under the inguinal ligament the SAFN is situated laterally to the location of the maximal pulsation of the femoral artery, and it has been shown that the nerve is reasonably easy to reach with a needle electrode in this area (Ertekin, Saphenous Nerve Conduction in Man, 1969). The area of the inguinal ligament allows for sensing that assesses parameters and locations lower in the leg in the stimulation of the SAFN or other nerves of the leg. Further, it may serve as a site of stimulation for nerves that travel down the leg.

Figure 14:
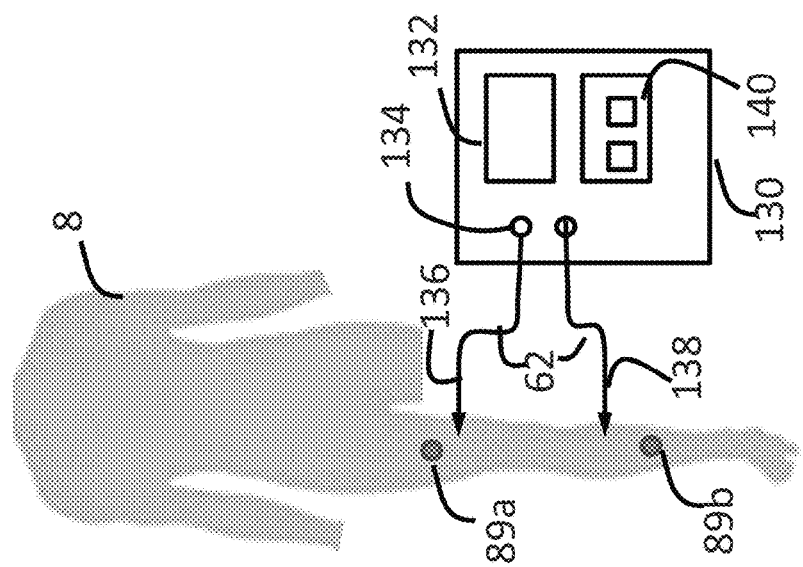
FIG. 14 shows an assessment system used to assess stimulation sites and protocols.

FIG. 14, shows a stimulation assessment system including a stimulation assessment device 130 for assessing parameters and locations of stimulation in a patient 8 has a display 132, ports 134 for connecting to electrodes for providing stimulation and sensing, a first electrode 136 located more rostral to a second electrode 138 or neurostimulator, both of which connect to conduits 62 to the ports 134. The stimulation assessment device 130, also has controllers 140. The assessment device can contain or control all the modules that have been described for the device 12, and which are shown in FIG. 2. The recording circuitry of the device 130 includes a separate channel to record a timing pulse or stimulation waveform for purposes of time-locking (trigger signal) and averaging the recorded neural signal. The recording electrode for the time locking channel is connected to the output of the stimulator (with appropriate attenuation circuitry) so that the stimulation waveform is recorded and can provide time-lock marker for averaging the post-stimulation neural response. Alternatively, a separate trigger channel can be used to record the trigger. Other schemas for obtaining time-locking are well known. The electrode 136 is understood to represent a monopolar, bipolar, tripolar, paddle electrode, or other configuration which can provide stimulation/sensing, and can include a ground, but is simplified to avoid cluttering of the figure.

In an embodiment, sensed data recorded from an electrode 136 at a more rostral site is used to determine whether stimulation provided in the lower leg elicits a nerve action potential. This detected evoked signal would provide confirmation (meet stimulation success criteria) that SAFN stimulation generates afferent neural volleys up to the lumbar spine which in turn leads to therapeutic treatment of OAB. In addition, sensing stimulation-evoked neural activity can be used to evaluate whether successful SAFN activation can be achieved with a candidate treatment location for TENS, percutaneous or implantable devices. For example, candidate anatomical locations in the lower leg can be electrically stimulated, and the sensed data can then be used to determine whether that site is appropriate for treatment using a TENS stimulator, percutaneous electrode 138, or implantable neurostimulator 89b. When the assessment device 130 measures time-locked evoked neural response from the recording electrode 136, it can achieve time locking by communicating (via communication module 52 of FIG. 2) with the implanted neurostimulator 89b to either receive data related to when a stimulation signal was provided or to control the neurostimulator to provide the stimulation pulses at selected times that allow for time-locking and averaging of the evoke neural impulses recorded rostrally. Assessment parameters can be modified so that stimulation (and assessment) parameters may be evaluated by the system in a closed loop manner, using algorithms, rules or control laws.

In an embodiment, an electrode 136 introduced at the level of the inguinal ligament is used for recording and assessing the effects of stimulating the SAFN. Sensing and evaluating sensed data from this electrode can allow stimulation parameters to be set. For example, this can be used to set a lower bound for the stimulus amplitude used during stimulation if this is sufficient to evoke response at this more rostral location. The sensing occurs by sensing module 50 and evaluation can be provided algorithmically by the control module 40 which performs signal conditioning, averaging, spectral analysis, etc. on the recorded data and shows the user result analytics on the display 132, and/or the assessment of the location or stimulus parameters is assessed by a human evaluating the displayed averaged evoked response waveform data.

In an embodiment, a patient's subjective sensory response can be used to determine threshold stimulation parameters for evoking paresthesia. The stimulation intensity can then be set at, above, or slightly below this level to provide therapy. When stimulation is provided with sufficient frequency (e.g., daily rather than weekly or monthly) the "strength" of the stimulation may be set lower than when more infrequent stimulation serves as therapy. If the stimulation is set to occur during therapy at, or slightly below the estimated nerve recruitment threshold as reflected by a subject's sensory report, the stimulation parameters used should still be sufficient to evoke a change that travels rostral to the site of stimulation. Using recorded data can validate that stimulation is adequate to evoke a neural response that is recordable higher in the leg. Additionally, a patient may report paresthesia and nerve recruitment is sufficient. However, recorded activity can assist not only in ensuring an adequate nerve recruitment, but can allow for adjusting stimulation parameters to produce a more discrete (in time), larger, or other desired feature in the evoked activity that is associated with producing improved therapy.

Using objective measured neural evoked potentials rather than subjective sensation, may lead to improved stimulation, by allowing for more accurate, quantitative, quicker or other advantages in some patients. Two other advantages of this method are providing improved screening of candidate patients who will respond to SAFN stimulation therapy and allowing the surgeon to confirm correct placement of implantable SAFN electrode during surgery (this is especially relevant if the patient is given anesthesia). The assessment device 130 and methods is helpful in cases where a patient is not able to reliably report a subjective sensation in response to stimulation since it provides an objective manner of measuring the upstream evoked activity.

Figure 15:
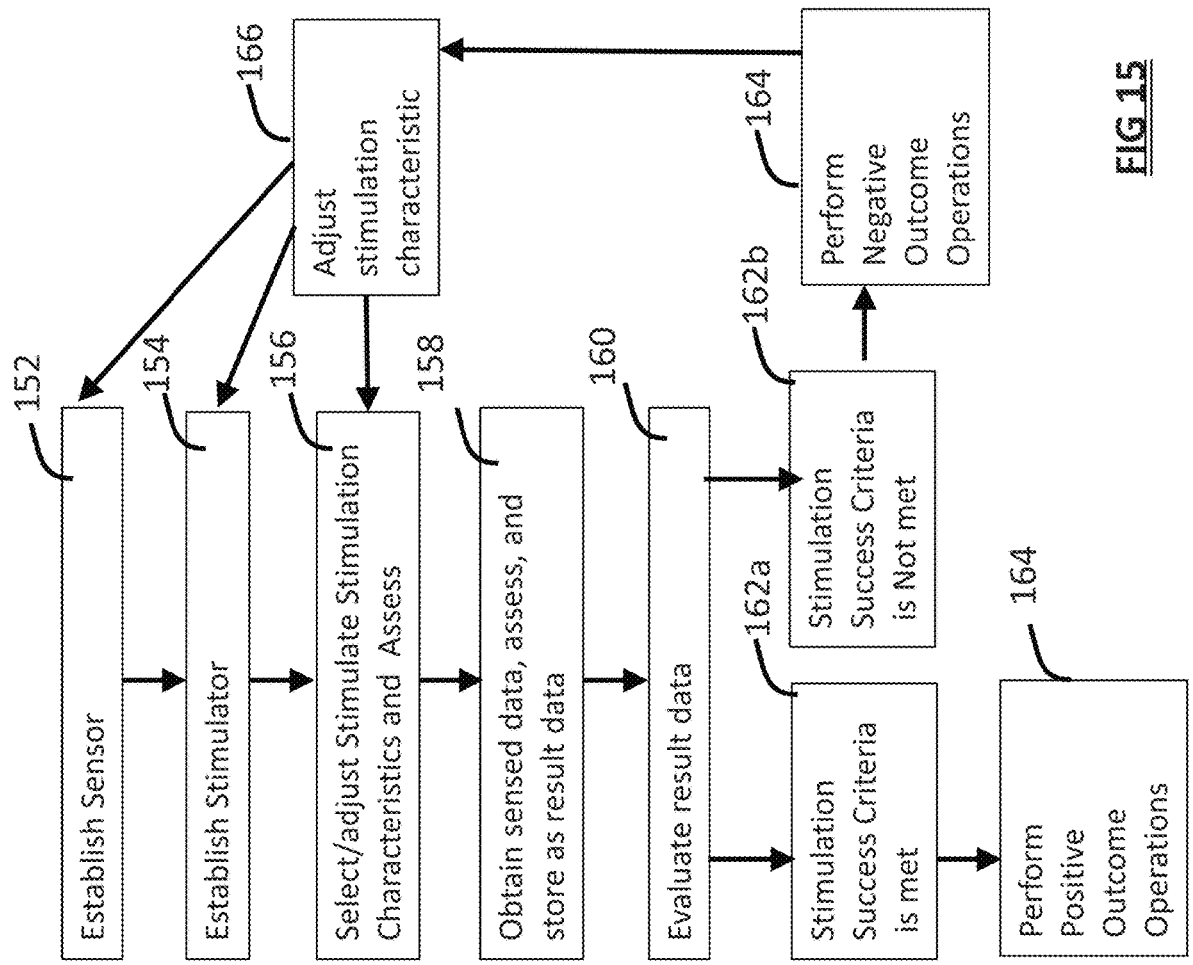
FIG. 15 shows an assessment method used to assess stimulation sites and protocols.

In an embodiment, as shown in FIG. 15, a first step of a method includes establishing a sensor 152 such as a needle electrode at a first site (such as a subject's inguinal ligament) that is rostral to a second site. In the next step a stimulator is positioned and a nerve (the SAFN or other nerve target) is stimulated at a second site 154. For example, the stimulator may be positioned at or below the level of the knee using a) stimulation parameter ranges that are selected for treatment of a disorder or b) stimulation parameter settings that are considered useful in assessing a candidate stimulation characteristic such as location, parameter or protocol. When the inhibition of bladder activity is intended the stimulation protocol can use a pulse frequency of between 1 and 25 Hz, and a characteristic such as pulse amplitude may be assessed. At least one stimulation characteristic is selected or adjusted and used for stimulation 156. The sensed data (e.g., neural, physiological, muscle) are recorded as result data which is also stored 158 is raw or summary format or which can simply be assessed to create result data. The processing of sensed data into result data can include for example, signal conditioning, frequency or time frequency analysis, algorithmic assessment of the data, manual assessment of the data, and time-locked averaging. In the next step the result data are assessed 160 algorithmically, visually, or otherwise assessed by a user. In this step 160 result data can be compared to reference criteria to determine at least one stimulation success criterion has been met. For example, a sensory evoked response is recorded at the electrode site that meets a treatment criterion. A stimulation success criterion used in step 160 can be defined simply as the presence of an evoked response or averaged evoked response. This can be measured or visually assessed. The stimulation success criterion can utilize a measurement of relative, normalized, or absolute amount of neural activity. The measure may be related to amplitude, spectral power, correlation, coherence, or other measure computed upon the neural response data (which may preferably be time-locked). The measure can be a change-relative to pre-stimulation sample that exceeds a defined amount. The stimulation success criterion can provide evidence that an evoked response has traveled proximal or distal from the stimulation site.

If the criterion is met 162a then the method leads to positive outcome operations 164 such as ending the assessment procedure and using at least one of the stimulation characteristics that met a stimulation success criterion to provide therapy. Alternatively, even if stimulation success criteria are met 162a, the method may return to step 166 where a characteristic is selected or adjusted and the steps of the method are repeated. This is useful when multiple successful characteristics are used or evaluated by the method. For example, a positive outcome operation 164 may entail selecting the characteristic that produced the largest evoked response to a selected amplitude of stimulation. When the characteristic evaluated is electrode position, the site which evoked the largest neural response may be selected for use during treatment. Alternatively, the candidate site which produced an evoked neural response to the lowest amplitude of stimulation may be selected for use during therapy.

If the criteria are not met then negative outcome operations occur. Negative outcome operation can include adjusting a stimulation characteristic 166 such as a stimulation parameter related to amplitude. Re-assessment then again occurs in step 156. Alternatively, a different sensing 152 or stimulation 154 site (or both) is selected and the method is repeated.

If at least 1 stimulation success criterion is met, then the recorded neural response data can be used to adjust the stimulation parameters that are used during therapy. For example, positive outcome operations may use the data to set minimum and maximum amplitudes of the stimulation waveform, to select at least one candidate stimulation site to be used during therapy, or to confirm that a patient is a successful candidate for electrical therapy (in a screening protocol). Stimulation amplitude may be set at the evoked response threshold or at a selected amount above threshold. A treatment criterion, symptom severity, or other considerations can also be used to set the minimum and maximum values of stimulation parameters used during the provision of therapy.

In an embodiment, an electrode 136 is used for stimulating the SAFN and is introduced at a candidate position at the level of the inguinal ligament. To assess this candidate stimulation site, the SAFN is stimulated at a first site lower in the leg and data is sensed at the candidate site in the inguinal region to assess the candidate site. If stimulation success criteria are met (e.g., if an evoked potential is successfully recorded from the candidate site at the level of the inguinal ligament) then a stimulator can be implanted to stimulate the SAFN at this more rostral site. Further, after the stimulator is implanted stimulation parameters can be selected as those which produce a subjective sensation from the patient. Alternatively, measurements downstream at the site lower in the leg can be used to assess the stimulation of the more anterior site (i.e., antidromic potentials can be measured). Conversely, measures "upstream" from the stimulation site may be assessed by measuring changes in bladder activity, bladder pressure, or other relevant measure as obtained from sensed data of one or more sensors (or otherwise). Sensors may be implanted, external to the patient, or may be inserted vaginally or anally to obtain physiological or other data in an acute manner. In an embodiment, the method also includes recording thigh muscle EMG to ensure minimal spillover.

Since recording the distal nerve action potential does not mean the patient will tolerate the therapy, such EMG assessment is also useful in creating patient comfort.

In an embodiment, only sites at or below the knee are stimulated and sites which are downstream from a stimulation site can be used to assess candidate sites or parameters. For example, when the implant site is located below the knee, a needle electrode can be inserted at the nerve branch near the ankle and sensory nerve evoked potentials can be assessed to validate that stimulation at the implant site produces evoked activity.

In an embodiment, conduction velocity along a peripheral nerve can be determined during an assessment procedure and if the results are abnormal then the patient may be excluded as a candidate for peripheral therapy, including OAB therapy. This result can suggest peripheral neuropathy which may hinder a successful response to subsequently provided therapy.

In an embodiment, TENS stimulation of lower leg SAFN network is assessed by evaluating sensed activity from a site at the level of the inguinal ligament to determine successful or unsuccessful SAFN network recruitment.

In an embodiment, stimulation is provided at the level of the inguinal ligament, and recording is done using the SAFN or other target in the lower leg to confirm successful nerve recruitment in response to stimulation. The stigmatic electrode is inserted at the inguinal ligament about 0.5 to 1.5 cm lateral to the maximum pulsation of the femoral artery. The indifferent electrode can be inserted 1.5 to 3.0 cm more laterally. A circular ground electrode may also be placed between the electrodes at the inguinal ligament and in the vastus medialis muscle. These three electrodes are represented as electrode 136 in FIG. 14. The stimulation parameters used during the assessment procedure can be different than that used to provide therapy stimulation. For example, a stimulus duration of 0.2 msec square pulse at 40 to 60 mA can be used and the position of the recording electrode is adjusted to a position which gives the lowest threshold. In an embodiment, one or more stimulation assessments at the level of the inguinal ligament can be used to verify candidate locations subsequently used for implant of a neurostimulator (rather than implanting at a location in the lower leg). In other words, rather than being a diagnostic area for determining effective stimulation sites and parameters for sites at or below the knee, the sites below the knee can be used to determine the best site near the inguinal ligament or underneath the Sartorius muscle (e.g., mid-thigh region) for providing stimulation of a nerve such as the SAFN in the treatment of a disorder such as OAB. Similarly, when the PTN is stimulated confirmation can occur at a rostral site such as near the popliteal fossa.

In an embodiment, SAFN stimulation uses two electrodes oriented approximately along an axis that is perpendicular to the long axis of the leg. These may be positioned at or just below the lower edge of the patella on the medial aspect of the leg, using either surface electrodes or two electrodes of an implanted neurostimulator to stimulate the infrapatellar branch. This stimulator arrangement may decrease risk of calf muscle activation relative to positioning electrodes lower in the leg. Further, muscle activity artefact may contribute less noise to evoked neural response data recorded more proximately or distally. This stimulator arrangement may also improve comfort by avoiding stimulation of relatively larger portions of the SAFN network targeted by sites below the knee.

In an embodiment, cutaneous or needle electrodes are positioned at candidate positions located at or below the level of the knee to map candidate stimulation parameters and sites for subsequent provision of therapy (e.g., to assess candidate location for an implanted device).

Placement of electrode stimulators, especially for implantable systems can be mapped out using imaging data, physiological data, or patient report on sensation evoked by at least one level of stimulation provided at distinct locations (prior to or during surgery). In an embodiment, a first step of a method includes stimulation with cutaneous or percutaneous electrodes at candidate locations. One or more sites which produce a stronger nerve recruitment sensation (or evoke nerve recruitment sensation at a lower threshold level of stimulation) can then be selected for use during implantation or for assessment using evoked neural activity methods. Site(s) that produces the largest growth curve in a measured response (e.g., evoked response amplitude or subject report of sensation) per unit of increase in stimulation may be selected for use.

In an embodiment, rather than stimulation at the level of the inguinal ligament, pelvic disorders including OAB are treated more rostrally using stimulation of the superior or lateral cluneal nerves that innervate the skin of the upper buttocks and are terminal ends of lateral rami of the posterior rami of lumbar spinal nerves (L1, L2, L3). Additionally, the rami can serve as stimulation targets using TENS, eTENS, or implanted neurostimulators.

Assessment/Re-Assessment of Stimulation Parameters.

In an embodiment, the control module of the device 12 is programmed to implement a user calibration routine that determines the maximum stimulation level that is also comfortable for the patient. The routine can assess or calculate this level for patient positions and states such as supine, prone, standing, sitting, sleeping, and walking. These distinct parameters value sets guide stimulation therapy based upon user body position and/or activity level as determined by a clock, accelerometer, or other sensor.

In embodiments, assessment of initial treatment waveform characteristics is followed by re-assessment of therapy at later times. The patient experience may change over time relative to start of a therapy session. A patient may become less sensitive to stimulation due to habituation or the impedance may increase (or decrease). For example, re-assessment at one or more times during a session includes having a subject press a button to indicate the threshold of pain to a stimulus that ramps up in intensity. The re-assessment is preceded by alerting a subject, or the subject can trigger re-assessment by pressing a button. In an embodiment, at a selected elapsed time, a re-assessment protocol subroutine causes the stimulator to transition from continuous stimulation to a waveform with a periodic pattern of ON and OFF intervals. For example, five ON intervals of 1-second are interspersed by intervals lasting 0.5 seconds where no stimulation occurs. This type of non-continuous stimulus can cause the user to pay attention to stimulus level and determine if re-assessment is desired.

Alternatively, the re-assessment protocol test causes the stimulator to change the stimulation waveform to an "oscillation mode" so that the amplitude of the stimulation waveform decreases to a lower level (e.g. 50%) of the selected stimulation intensity, and then ramps back up, rather than the stimulation being continuous. For example, 5 to 15 intervals downward and upward ramping can occur where the downward ramp occurs over a 0.5 to 2 second period, and follows a linear or sinusoidal function, followed by an upward ramp. The oscillation mode may also use a maximum intensity that is 5% to 20% above the intensity used to provide continuous stimulation since non-continuous stimulation patterns may allow a higher intensity to be used without causing discomfort compared to the amplitude tolerated with continuous stimulation. Oscillating functions can also be used to provide therapy for users who prefer dynamic rather than continuous stimulation.

An assessment procedure may include assessing the location and/or stimulation parameters (e.g., the intensity) to be used during therapy. The assessments can be initiated by the user pressing a "start" button 106 of the control system a certain number of times, or different assessment procedures can be initiated by the user pressing different buttons on the control system or by using a graphical user interface provided on the control system or via a remote device connected to the control system. After assessment is completed then therapeutic stimulation is initiated by pressing a "start" button 114 of the control system which causes stimulation to occur for a selected interval such as 30-60 minutes. When the therapy session terminates, or is terminated by the user, the stimulation is halted and the TENS apparatus 8 is removed from the individual.

Although a one-button interface may be used to start, stop, and pause device operations (using different durations or patterns of button presses) using two or more buttons may facilitate patient-device interaction. At least 2 other buttons can be provided to allow a user to increase or decrease stimulation intensity. Rather than using physical buttons, user-device operation can also occur wirelessly using a controller which may be a user device 32, realized as customized hardware or within a user's smart-phone.

TENS stimulation for various disorders typically occurs at stimulation intensity that produces a "strong but not painful" sensation. In the treatment of OAB, it has not been clearly shown that stronger stimulation produces larger benefits, although data is suggestive at least for some frequencies. It is likely that using stimulation that is above sensation threshold but below an intensity that is not tolerable for a patient is suitable for treatment of OAB. Stimulation that is near the maximum tolerable level may not be necessary and may not provide increased benefit compared to lower stimulation levels. Several methods may be used to select appropriate stimulation locations and stimulation parameters used during therapy. In an embodiment these may be selected during an initial visit as determined by a doctor in a clinic. In another embodiment these can be determined manually by a patient. In another embodiment, this can occur in a semi-automatic manner where some steps are done by the patient and some are done automatically by the device. Lastly, in an embodiment these can be determined by patient and system interaction where the system provides auditory, visual, or audio-visual instructions that allow the patient to set up and use the system correctly.

In an embodiment the device 12 can map a patient's pain tolerance by stimulating the patient at various stimulation strengths and having the patient input the level of perceived pain on a 10-point scale where 1 is just being able to feel the elecrotactile stimulation, 5 is comfortable, 7 is uncomfortable and 10 is not tolerable.

Electrode Spacing and Geometry.

In experiments conducted by the inventors using both TENS and PENS approaches, on female overactive bladder patients greatest success in stimulation the SAFN has been obtained by placing a first electrode between the proximal-anterior boundary of the calf muscle and the tibia and the second electrode placed 2-3 inches more distally (mid-calf) so that its center is located at the boundary between the tibia and the boundary of the calf muscle. The success of this approach is supported by an article entitled "Categorizing the Distribution of the Saphenous Nerve in Relation to the Great Saphenous Vein" by Wilmot & Evans Clinical Anatomy 26:531-536 (2013), which shows 3 distributions (types A-C) of the SAFN and the great saphenous vein (GSV), and indicates that the main branch of the SAFN follows the palpable ridge between the tibia and the medial calf muscle. Because the SAFN near, and at, the level of the knee is located medially, an embodiment of an electrode array has both a vertical spacing between at least two electrodes and the more distal electrode location is positioned anteriorly and while the proximal electrode is positioned more medially, when the band is worn by the patient. This "diagonal" arrangement should allow the stimulation path to entrain the SAFN.

In an embodiment, the SAFN can be stimulated at the medial aspect of the knee using 2 electrodes spaced 2 to 3 centimeters apart, aligned perpendicularly with the longitudinal aspect of the leg to provide a relatively superficial path of energy. This configuration is convenient from a device design viewpoint and may provide shallow stimulation. In an embodiment, this configuration is positioned to restrict stimulation to the infrapatellar branch of the SAFN. Alternatively, it may be preferable to stimulate a larger portion of the SAFN. Positioning the second electrode about one-third down the length of the tibia may provide a larger response of the main branch rather than only stimulating the infrapatellar branch. The use of electrodes near the knee versus electrodes that span a larger section of the patient's leg may provide a tradeoff between neural recruitment (symptom improvement) and patient comfort. When stimulation is provided for a long period of time, such as while the patient is asleep, using a lower amplitude stimulus, or stimulating a smaller portion of the SAFN may still provide sufficient therapy benefit.

In an alternative embodiment, SAFN stimulation is provided to treat a pelvic floor disorder both at a site positioned for stimulating the infrapatellar branch or at the anterior SAFN branch which runs anteriorly near the medial malleolus. Stimulation of one or both targets may elicit a noticeably weaker sensation (which may be desired in some sensitive patients), while still providing pelvic floor modulation sufficient for therapy benefit. However, it is possible that the decrease in the number of SAFN fibers at these two SAFN sites may lead to smaller therapeutic benefit than stimulation along the main branch.

Stimulation Parameters

In an embodiment, a stimulation protocol for treatment of a pelvic floor disorder has a frequency range selected to be from 5 to 25 Hz. In an additional embodiment, used for treating pain, the protocol uses a biphasic waveform with alternating leading phase, symmetrical, rectangular pulses. The pulse duration can be set between approximately 200 to 400 μsec having a frequency that is set at between 60 Hz and 100 Hz. The stimulation frequency, pulse width, or other parameter may vary within that range in various known manners (e.g., oscillating, random or other variation in instantaneous frequency) that may be pre-set or manually selected by the patient. In an embodiment, the maximum current density can be set to be approximately 1 mA/cm (using a 500Ω load), but this will vary depending upon electrode size, geometry, and inter-electrode spacing. In various embodiments a maximum current density can be regulated in order to deter harm to patient when used on a particular area of the body or for a selected duration.

Pulse strength (duration or amplitude can increase energy used in the simulation protocol. In a TENS device, an electrical circuit typically generates stimulation according to specified characteristics. The pulse waveform specifications can include intensity (mA), frequency or repetition rate (Hz), pulse duration (μsec), duty cycle, waveform (square, sinuosoidal, triangular), and polarity of pulses (monophasic, biphasic). The waveform protocol may also define intervals between stimulation ON periods and length of the treatment session (minutes or hours). When one or more pairs of electrodes, are placed on the patient's skin then the protocol can assign different waveforms to different electrode contacts at different moments in time, and can be used to provide interferential stimulation patterns. By varying the intensity, duration, width, frequency, inter-pulse interval, and other characteristics of the stimulation pulses both the clinical benefit, effects, and subjective "intensity" of TENS can adjusted.

During the stimulation protocol or an assessment protocol, the pulses can occur continuously, may be periodic, may occur in periodic bursts, or may be continuous but may vary in amplitude according to a slowly varying envelope (e.g. 5 second decrease in amplitude followed by 5 a second increase). The use of a discontinuous or varying stimulus can be advantageous in allowing a user to assess the effects of stimulation. For example, it may be difficult to confirm a sensation of radiation away from TENS electrode (e.g. down their leg and towards their ankle) using continuous stimulation. In contrast, a protocol where stimulation transitions from below to above sensory threshold may allow a user to repeatedly assess the sensation evoked by stimulation that successfully recruits the SAFN. In several subjects who had difficulty assessing the distance, or presence, of a radiation of sensation away from the site of stimulation, varying the stimulation signal above and below the nerve recruitment threshold enabled the subjects to more easily recognize the stimulation-evoked sensations.

The systems and methods disclosed herein are often embodied using a TENS system. There are also embodiments related to implantable and percutaneous stimulation and sensing. There are also systems where the transcutaneous stimulation is magnetic rather than electrical. Features, system components and methods disclosed for external, percutaneous, and implantable embodiments are understood to apply to these other embodiments. System modules that are described for the stimulator may be incorporated into the patient device or other system component. The illustrated embodiments are understood to be non-limiting with respect to obvious variations that accomplish the same advantages.

What is claimed is:

1. A method for providing a neurostimulation treatment to a patient including:

a. positioning at least a first sensor at a first location in a patient to provide sensing;

b. positioning at least a first stimulator, a second stimulator and third stimulator at at first, second and third locations below the waist of the patient to provide operationally dependent integrated stimulation between said first, second and third stimulators of a target peripheral nerve across the stimulators;

c. selecting or adjusting a stimulation parameter of a stimulation protocol;
d. operating a stimulation assessment device to provide stimulation according to a stimulation protocol to the at least first stimulator and obtaining sensed neural data of evoked neural responses;
e. determining from the sensed neural data whether at least one stimulation criterion has been met including:
   (1) evaluating and classifying a characteristic of the neurostimulation treatment protocol as successful where the at least one stimulation success criterion is met, or,
   (2) evaluating and classifying a characteristic of the neurostimulation treatment protocol as unsuccessful where no stimulation success criterion is met and adjusting the characteristic of the neurostimulation treatment protocol by repeating steps b through e sequentially until at least one stimulation success criterion is met; and,
f. subsequently providing treatment of a pelvic floor disorder in the patient using a neurostimulation treatment protocol having at least one selected characteristic classified as successful in step e.

2. The method of claim 1 wherein the characteristic of neurostimulation treatment is selected to be at least one of the group of: stimulation parameter, stimulation protocol, and at least one stimulation site.

3. The method of claim 1 wherein the step of positioning at least a first sensor at a first location in a patient to provide sensing includes positioning the sensor within an inguinal region and positioning at least a first stimulator at a second location includes positioning the stimulator to stimulate saphenous nerve of the patient between the level of the knee and the bottom of the calf muscle.

4. The method of claim 1 wherein the step of positioning at least a first sensor at a first location in a patient to provide sensing includes positioning the sensor adjacent to an inguinal ligament and positioning the at least first stimulator at a second location includes positioning the at least first stimulator to stimulate a saphenous nerve of the patient.

5. The method of claim 1 wherein the step of positioning at least a first sensor at a first location in the patient to provide sensing further includes a confirmation step to ensure that the at least first sensor is capable of sensing stimulation provided to at least one location below the level of the knee, the confirmation step comprising positioning the at least first sensor adjacent to or on a saphenous nerve of the patient between the level of the knee and the bottom of the calf muscle, and positioning at least a second stimulator at a second location includes positioning the at least stimulator adjacent to or on an inguinal ligament.

6. The method of claim 5 wherein the characteristic of a neurostimulation treatment is the position of a stimulation electrode which stimulates the saphenous nerve located adjacent to the inguinal ligament.

7. The method of claim 1 wherein the step of positioning at least a first sensor at a first location in a patient to provide sensing includes positioning the at least first sensor in the area rostral to the at least first stimulator and, positioning the at least second stimulator at a second location in a leg of the patient and includes positioning the at least third stimulator on a tibial or a post-tibial nerve between a knee and a medial malleolus of the patient.

8. The method of claim 1 wherein operating a stimulation assessment device to provide stimulation according to the stimulation protocol includes communicating with an implantable neurostimulator device with respect to the timing of neurostimulation pulses in order to derive evoked neural responses.

9. The method of claim 1 wherein at least one stimulation success criterion includes the detection of an evoked response in sensed neural response data.

10. The method of claim 1 wherein in step (e) the at least one characteristic that has been classified as successful includes selecting the characteristic that produced the largest evoked response.

11. The method of claim 1 wherein in step (e) the at least one characteristic that has been classified as successful includes selecting a location for stimulation having a lowest threshold for obtaining an evoked neural response.

12. The method of claim 1 in step (e) wherein at least one stimulation success criterion includes at least one of: a criterion related to a relative measure of neural activity, normalized measure of neural activity, absolute or relative change of a measure of amplitude, spectral power, correlation, coherence as computed upon the neural response data.

13. The method of claim 1 wherein the characteristic of a neurostimulation treatment is a stimulation parameter related to pulse rate frequency.

14. The method of claim 1 wherein the characteristic of a neurostimulation treatment is a stimulation parameter related to pulse amplitude.

15. The method of claim 1 wherein the characteristic of a neurostimulation treatment is a positional location of a stimulator of an implanted neurostimulator.

16. The method of claim 1 wherein the step of operating a stimulation assessment device to provide stimulation according to a stimulation protocol at the at least first stimulator and sensing sensed neural data, includes using a stimulation protocol parameter that has previously been shown to successfully stimulate a nerve as indicated by a behavioral response of the patient.

17. The method of claim 1 wherein the step of selecting at least one characteristic that has been classified as successful and using at least one characteristic to provide treatment of a pelvic floor disorder in the patient, includes using the at least one characteristic to set the minimum level used during treatment as the minimum level of stimulation needed to evoke a neural response in the patient.

18. The method of claim 1 wherein the step of selecting at least one characteristic that has been classified as successful and using that characteristic to provide treatment of a pelvic floor disorder in the patient, includes using the at least one characteristic to seta the maximum level of stimulation provided by said at least first, second and third stimulators.

19. The method of claim 1 wherein the target nerve is the saphenous nerve.

20. The method of claim 1 wherein the target nerve is the posterior tibial nerve.

* * * * *